US008753408B2

(12) United States Patent
Emmerling et al.

(10) Patent No.: US 8,753,408 B2
(45) Date of Patent: Jun. 17, 2014

(54) REDUCTIVE DECOLORATION OF KERATIN-CONTAINING FIBERS

(75) Inventors: Winfried Emmerling, Tomesch (DE); Holger Bartels, Hamburg (DE); Inge Neubueser, Hamburg (DE)

(73) Assignee: Henkel AG & Co. KGaA, Dusseldorf (DE)

( * ) Notice: Subject to any disclaimer, the term of this patent is extended or adjusted under 35 U.S.C. 154(b) by 905 days.

(21) Appl. No.: 12/709,664

(22) Filed: Feb. 22, 2010

(65) Prior Publication Data

US 2010/0146710 A1  Jun. 17, 2010

Related U.S. Application Data

(63) Continuation of application No. PCT/EP2008/060685, filed on Aug. 14, 2008.

(30) Foreign Application Priority Data

Aug. 23, 2007  (DE) .......................... 10 2007 039 954

(51) Int. Cl.
*D06L 3/00* (2006.01)
*A61K 8/30* (2006.01)

(52) U.S. Cl.
USPC ................... 8/404; 8/127.51; 8/127.6; 8/110; 252/188.2; 424/170.1

(58) Field of Classification Search
USPC .................... 8/107, 110, 127.51, 127.6, 404; 252/188.1, 188.2; 424/170.1
See application file for complete search history.

(56) References Cited

U.S. PATENT DOCUMENTS

| 4,524,787 | A | * | 6/1985 | Khalil et al. ................... 132/204 |
| 4,746,322 | A | * | 5/1988 | Herlihy .............................. 8/405 |
| 4,865,774 | A | | 9/1989 | Fabry et al. |
| 4,931,218 | A | | 6/1990 | Schenker et al. |
| 5,294,726 | A | | 3/1994 | Behler et al. |
| 5,318,733 | A | | 6/1994 | Carduck et al. |
| 5,516,507 | A | | 5/1996 | N'Guyen et al. |
| 5,773,595 | A | | 6/1998 | Weuthen et al. |
| 5,998,537 | A | | 12/1999 | Good et al. |
| 6,106,579 | A | | 8/2000 | Kunz et al. |
| 6,156,077 | A | * | 12/2000 | Shibata et al. ..................... 8/406 |
| 6,214,873 | B1 | * | 4/2001 | Adachi et al. ................. 514/546 |
| 6,743,419 | B1 | | 6/2004 | Shander et al. |
| 2004/0146478 | A1 | * | 7/2004 | Queralt et al. ............. 424/70.27 |
| 2004/0241099 | A1 | * | 12/2004 | Popp et al. ....................... 424/45 |
| 2005/0123487 | A1 | | 6/2005 | Spadini et al. |
| 2007/0241306 | A1 | * | 10/2007 | Wehner et al. .................. 252/67 |
| 2008/0025938 | A1 | * | 1/2008 | Cassier ......................... 424/70.5 |
| 2009/0156485 | A1 | * | 6/2009 | Barg et al. ......................... 514/12 |
| 2009/0276964 | A1 | * | 11/2009 | Asada ................................ 8/102 |
| 2010/0015070 | A1 | * | 1/2010 | Bollschweiler et al. ........ 424/59 |

FOREIGN PATENT DOCUMENTS

| AU | 730455 B2 | 3/2001 |
| CA | 2066226 A1 | 3/1991 |
| DE | 102004045353 A1 | 4/2006 |
| EP | 0874017 A2 | 10/1998 |
| WO | 2008012733 A2 | 1/2008 |

\* cited by examiner

*Primary Examiner* — Tri V Nguyen

(74) *Attorney, Agent, or Firm* — Ingrassia Fisher & Lorenz, P.C.

(57) ABSTRACT

The invention relates to compositions comprising a combination of (a) at least one organic compound which carries at least one thiol group and at least one optionally derivatized carboxyl group, for example L-cysteine, and (b) at least one organic compound selected from the group which is formed from cyclic, organic carbonates, glycerol and its derivatives and $C_4$-$C_{12}$ fatty acid dimethylamides. Using these low-odor compositions it is possible to reductively decolor colored keratin-containing fibers, in particular human hair, in a rapid and effective manner.

8 Claims, No Drawings

REDUCTIVE DECOLORATION OF KERATIN-CONTAINING FIBERS

CROSS REFERENCE TO RELATED APPLICATIONS

The present application is a continuation of International Application No. PCT/EP2008/060685 filed 14 Aug. 2008, which claims priority to German Patent Application No. 10 2007 039 954.7 filed 23 Aug. 2007, both of which are incorporated herein by reference.

The invention relates to agents comprising a combination of (a) at least one organic compound having at least one thiol group and at least one optionally derivatized carboxy group and (b) at least one organic compound selected from the group formed by cyclic organic carbonates, glycerol and its derivatives and $C_4$-$C_{12}$ fatty acid dimethylamides. Likewise, use of these agents for decoloration of keratin-containing fibers (e.g., human hair) and a method for decoloration of keratin-containing fibers are the subjects of this invention.

In dyeing, the dye is transferred to substrates by adsorption onto the surface, diffusion, formation on and/or in the substrate, and/or by chemical bonding. Natural dyes were first used (e.g., purple or scarlet). Due to rapid scientific advances, synthetic dyes tailored to specific application have become accessible. For dyeing paper, textiles or keratin-containing fibers, for example, typically substantive dyes or oxidative dyes are used. Oxidative dyes are formed by oxidative coupling of one or more developer components with one another or with one or more coupler components. Coupler components and developer components are also known as oxidative dye precursors. Oxidative coupling preferably takes place during the dyeing operation so that the dye precursors can diffuse into the substrate, with the dye formed in the substrate. Because of the size of the resulting dye molecule, washing it out of the substrate is difficult.

Primary aromatic amines having an additional free or substituted hydroxy group or amino group in para- or ortho-position, diaminopyridine derivatives, heterocyclic hydrazones, 4-aminopyrazolone derivatives and 2,4,5,6-tetraminopyrimidine and its derivatives are generally used as developer components.

Specific representatives include p-phenylenediamine, p-toluoylenediamine, 2,4,5,6-tetraminopyrimidine, p-aminophenol, N,N-bis-(2hydroxyethyl)-p-phenylenediamine, 2-(2,5-diaminophenyl)ethanol, 2-(2,5-diaminophenoxy) ethanol, 1-phenyl-3-carboxyamido-4-aminopyrazol-5-one, 4-amino-3-methylphenol, 2-aminomethyl-4-aminophenol, 2-hydroxymethyl-4-aminophenol, 2-hydroxy-4,5,6-triaminopyrimidine, 2,4-dihydroxy-5,6-diamino-pyrmidine, 2,5,6-triamino-4-hydroxypyrimidine and 4,5-diamino-1-(2-hydroxyethyl)pyrazole.

Coupler components are usually n-phenylenediamine derivatives, naphthols, resorcinol and resorcinol derivatives, pyrazolones, m-aminophenols and substituted pyridine derivatives. Suitable coupler substances include α-naphthol, 1,5-, 2,7- and 1,7-dihydroxynaphthalene, 5-amino-2-methylphenol, m-aminophenol, resorcinol, resorcinol monomethyl ether, m-phenylenediamine, 2,4-diaminophenoxyethanol, 2-amino-4-(2-hydroxyethylamino)anisole (Lehmann's blue), 1-phenyl-3-methylpyrazol-5-one, 2,4-dichloro-3-aminophenol, 1,3-bis-(2,4-diaminophenoxy)propane, 2-chlororesorcinol, 4-chlororesorcinol, 2-chloro-6-methyl-3-aminophenol, 2-methylresorcinol, 5-methylresorcinol, 3-amino-6-methoxy-2-methylaminopyridine and 3,5-diamino-2,6-dimethoxypyridine.

Substantive dyes generally refer to dyes which are prepared before dyeing and are absorbed onto the substrate. Important representatives of this class of dyes include triphenylmethane dyes, azo dyes, anthraquinone dyes or nitrobenzene dyes, each of which may have cationic or anionic groups.

In dyeing, removal of dyes constitutes an important technical field. This generally refers to the removal of dyes or printings by washing out, chemical alteration or destruction of the dyestuff. Oxidative or reductive decoloration of dyed materials is used in decoloration of textiles or hair in particular.

Oxidative decoloration often leads to good results in removal, but the structure of the substrate may be chemically altered due to the strong oxidative effect of the oxidizing agent used for decoloration. This is associated with an unwanted physical change in the substrate. For example, textile or hair may become brittle or even break, particularly with repeated decoloration. Visual impression, tactile sensation and also stability of the substrate are therefore negatively influenced.

Reductive decoloration agents have less influence on substrate structure, particularly with respect to the structure of keratin-containing fibers. Reductive decoloration agents cause hardly any decoloration of the natural hair color, but have a reductive effect only on dyes applied by synthetic dyeing. Thus, there is hardly any lightening of the hair.

EP-A1-943 316 relates to use of compounds containing thiol groups in combination with α-ketocarboxylic acids in agents for decoloration of dyed hair.

DE-A-102004045353 relates to decoloration of dyed hair with the help of glycerol or derivatives thereof, organic carbonates or fatty acid dimethylamides.

However, decoloration agents found in the prior art require improvement in decoloration performance and reduction in application time.

The present invention provides reductive decoloration agents that permanently decolor substrates without any darkening. Substrate structure should be protected in the process. Furthermore, for cosmetic use, reducing agents used in the decoloration agents should be physiologically tolerable and toxicologically safe. Application time of the decoloration agents should be as short as possible.

The inventive agents and/or combination of active ingredients they contain are surprisingly excellently suited for accelerated and improved decoloration of dyed substrates such as paper, textile or keratin-containing fibers, in particular human hair. The inventive active ingredient combination is suitable in particular for decoloration of keratin-containing fibers in a manner that is protective of the fiber.

Keratin-containing fibers include wool, furs, feathers and hair, in particular, human hair.

Accordingly, the present invention therefore provides agents for reductive decoloration of keratin-containing fibers, in particular human hair, containing in a vehicle an active ingredient combination of—
  (a) at least one organic compound having at least one thiol group and at least one optionally derivatized carboxy group, and
  (b) at least one organic compound formed by (i) cyclic organic carbonates, (ii) glycerol and its derivatives, and/or (iii) $C_4$-$C_{12}$ fatty acid dimethylamides.

A derivatized carboxy group according to the invention refers to salts having a physiologically tolerable cation, carboxylic acid esters (—CO—O—R) and carboxylic acid amides (—CO—NH—R), where R is a saturated or unsaturated, linear or branched, cyclic or aromatic hydrocarbon radical which may optionally be substituted.

At least one compound suitable as a preferred compounds of component (a) is according to the following formula (I)

$$\text{HS—X—COOM} \tag{I}$$

wherein X is a saturated or unsaturated, linear or branched and aliphatic hydrocarbon structure, optionally substituted with thiol groups, carboxy groups, carboxylate groups, hydroxy groups, $NH_2$, $C_1$ to $C_6$ alkylamino, $C_1$ to $C_6$ dialkylamino and/or $C_1$ to $C_6$ hydroxyalkyl; and M is hydrogen, a $C_1$ to $C_8$ alkyl group, or an equivalent of a monovalent or polyvalent cation.

According to formula (I), preferably X is methylene, ethane-1,1-diyl, ethane-1,2-diyl, propane-1,1-diyl, propane-1,2-diyl, propane-1,3-diyl or butane-1,4-diyl, wherein each of these groups may optionally be substituted with thiol, carboxy, carboxylate, hydroxy, $NH_2$, $C_1$ to $C_6$ alkylamino group, or $C_1$ to $C_6$ alkylamino group.

In formula (I) X especially preferably is methylene, ethane-1,1-diyl, ethane-1,2-diyl, or propane-1,1-diyl, wherein each of these groups may optionally be substituted with carboxy, carboxylate, hydroxy, or $NH_2$ group.

X in formula (I) most especially preferably is ethane-1,2-diyl, wherein it is optionally be substituted with at least one of carboxy, carboxylate, hydroxy, or $NH_2$ group.

($C_1$ to $C_8$)-Alkyl radicals according to formula (I) (also in the ($C_1$ to $C_6$)-alkylamino groups and ($C_1$ to $C_6$)-dialkylamino groups) preferably are (and/or are preferably derived from) methyl, ethyl, propyl, isopropyl, n-butyl, sec-butyl, isobutyl, tert-butyl, n-pentyl, isopentyl, sec-pentyl, n-hexyl, 2-methylpentyl, n-heptyl, n-octyl, 6-methylheptyl, 2-ethylhexyl or 1,1,3,3-tetramethylbutyl.

If compounds of formula (I) are present as a salt, then M is an equivalent of a monovalent or polyvalent cation. Monovalent or polyvalent cation $M^{z+}$ having an atomic number z of one or more serves to compensate, for reasons of electroneutrality, for the single negative charge of the carboxylate fragment $—COO^-$ in formula (I), present in formation of the salt. The equivalent of the corresponding cation used is 1/z. The —COOM fragment of formulas (I) is the following group in the case of formation of a salt—

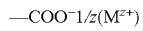

—$COO^- 1/z(M^{z+})$

In principle, all physiologically tolerable cations can be used as the monovalent or polyvalent cation $M^{z+}$. In particular, these include metal cations of the physiologically tolerable metals from groups Ia, Ib, IIa, IIb, IIIb, VIa or VIII of the periodic system of elements, ammonium ions and cationic organic compounds with a quaternized nitrogen atom. The latter are formed, for example, by protonation of primary, secondary or tertiary organic amines with an acid (e.g., with compounds of formula (I) in their acid form or by permanent quaternization of said organic amines). Examples of these cationic organic ammonium compounds include 2-ammonioethanol and 2-trimethylammonioethanol. M in formula (I) preferably is a hydrogen atom, an ammonium ion, an alkali metal ion, one-half equivalent of an alkaline earth metal ion or one-half equivalent of a zinc ion, especially preferably a hydrogen atom, an ammonium ion, a sodium ion, a potassium ion, ½ calcium ion, ½ magnesium ion or ½ zinc ion.

The inventive agent especially preferably contains as component (a) at least one compound chosen from at least one representative of the group formed by L-cysteine (acid or salt), D-cysteine (acid or salt), D,L-cysteine (acid or salt), cysteamine and acetylcysteine. Any stereoisomer of cysteine as an acid or salt is most especially preferably suitable.

Component (a) is preferably present in the inventive agents in an amount of 1 to 10 wt %, in particular from 1 to 5 wt %, each based on total weight of the agent.

According to the invention, preferably at least one cyclic carbonic acid ester is suitable as the cyclic organic carbonate of component (b)(i). These cyclic esters of carbonic acid are derived from 1,3-dioxolan-2-one and can be described by the following basic structure of formula (II-1)—

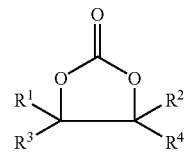

wherein radicals $R^1$, $R^2$, $R^3$ and $R^4$ are independently a hydrogen atom or organic radicals, in particular alkyl, alkenyl or alkylaryl, which may additionally be substituted with other groups, in particular hydroxy groups.

In the parent 1,3-dioxolan-2-one, radicals $R^1$, $R^2$, $R^3$ and $R^4$ of formula (II-1) each is a hydrogen atom. Also preferred suitable cyclic carbonic acid esters are derivatives of this parent substance wherein at least one of the radicals $R^1$, $R^2$, $R^3$ and $R^4$ of formula (II-1) is not a hydrogen atom. There are no limits to the structural variety here, so that mono-, di-, tri- and tetrasubstituted 1,3-dioxolan-2-ones of formula (II-1) are suitable for use within the scope of the invention.

In addition to unsubstituted 1,3-dioxolan-2-one, especially preferred derivatives are those of the following formula (II-2), which are monosubstituted in position 4—

wherein $R^1$ is a substituted or unsubstituted alkyl, alkenyl or alkylaryl radical.

Preferred $R^1$ radicals according to formula (II-2) include methyl, ethyl, n-propyl, isopropyl and hydroxymethyl, 1-hydroxyethyl and 2-hydroxyethyl radicals.

Consequently, especially preferred inventive agents contain as the 1,3-dioxolan-2-one derivative at least one compound of the above formula (II-2), wherein $R^1$ is a substituted or unsubstituted alkyl, alkenyl or alkylaryl radical, whereby in more preferred inventive agents the radical $R^1$ in formula (II-2) is chosen from methyl, ethyl, n-propyl, isopropyl and hydroxymethyl, 1-hydroxyethyl and 2-hydroxyethyl radicals.

Especially preferred 1,3-dioxolan-2-ones of formula (II-1) come from the group of ethylene carbonate ($R^1$, $R^2$, $R^3$ and $R^4$=H), propylene carbonate ($R^1$=$CH_3$ and $R^2$, $R^3$ and $R^4$=H) and glycerol carbonate ($R^1$=$CH_2OH$ and $R^2$, $R^3$ and $R^4$=H). Propylene carbonate is most especially preferably suitable.

Ethylene carbonate is a colorless crystalline compound which melts at 39° C. and boils at 238° C. Ethylene carbonate is readily soluble in water, alcohols and organic solvents, and can be synthesized on a large scale industrially from ethylene oxide and liquid $CO_2$. Propylene carbonate is a highly mobile liquid, clear as water, with a density of 1.2057 $gcm^{-3}$, a melting point of –49° C., a boiling point of 242° C. Propylene carbonate is also industrially accessible on a large scale by reaction of propylene oxide and $CO_2$ at 200° C. and 80 bar. Glycerol carbonate is accessible by transesterification of ethylene carbonate or dimethyl carbonate with glycerol, yielding ethylene glycol and/or methanol as byproducts. Another synthesis pathway involves reaction of glycidol (2,3-epoxy-1-propanol) with $CO_2$ under pressure in the presence of catalysts to form glycerol carbonate. Glycerol carbonate is a clear, highly mobile liquid which has a density of 1.398 $gcm^{-3}$ and boils at 125-130° C. (0.15 mbar)

Glycerol and/or at least one glyceride according to formula (III) are preferred glycerol compounds of component (b)(ii) that are preferably used in the sense of the invention: .

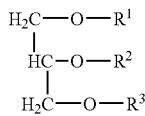 (III)

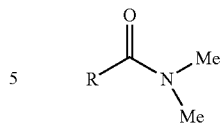 (IV)

wherein $R^1$, $R^2$ and $R^3$ independently of one another stand for a hydrogen atom or a $C_2$-$C_{10}$ acyl group, in particular independently of one another for a hydrogen atom or a ($C_2$ to $C_8$)-acyl group. Preferred $C_2$-$C_{10}$ acyl groups include acetyl, n-propanoyl, isopropanoyl, n-butanoyl, sec-butanoyl, n-pentanoyl, n-hexanoyl, n-octanoyl and n-decanoyl.

Compounds of formula (III) according to the invention include monoglycerides, diglycerides or triglycerides. It is especially preferable to use such formula (III) compounds that are liquid at room temperature and under atmospheric pressure. Most especially preferred glycerol compounds of component (b) are formed by glycerol and glycerol triacetate.

Within the scope of the invention, at least one compound of formula (IV) is suitable as component (b)(iii)— wherein R is a linear or branched ($C_4$ to $C_{12}$)-alkyl group.

R especially preferably is n-butyl, sec-butyl, n-hexyl, 2-ethyl-hexyl, n octyl, n-decyl or n-dodecyl.

Compounds of component (b) are preferably present in the inventive agents in an amount of 5 wt % to 50 wt %, in particular from 10 wt % to 30 wt %, each based on total weight of the agent.

Weight ratios of the compounds of formula (I) to the compounds of component (b) preferably amount to 1:2 to 1:20, in particular 1:3 to 1:10.

According to the invention, at least one of the following active ingredient combinations is especially preferably contained in the inventive agent—

|   | Component (a) | Component (b) |
|---|---|---|
| 1 | Cysteine and/or a salt thereof | at least one compound of formula (II-1) |
| 2 | Cysteine and/or a salt thereof | at least one compound of formula (II-2) |
| 3 | Cysteine and/or a salt thereof | ethylene carbonate |
| 3 | Cysteine and/or a salt thereof | glycerol carbonate |
| 4 | Cysteine and/or a salt thereof | propylene carbonate |
| 5 | Cysteine and/or a salt thereof | at least one compound of formula (III) |
| 6 | Cysteine and/or a salt thereof | glycerol |
| 7 | Cysteine and/or a salt thereof | glycerol triacetate |
| 8 | Cysteine and/or a salt thereof | at least one compound of formula (IV) |

A further improvement in decoloring power is obtained when the inventive agents also contain oxalic acid in addition to the active ingredient combination. This addition is preferably in an amount of 1 wt % to 5 wt %, based on total weight of the agent.

The following active ingredient combinations are preferred—

|   | Component (a) | Component (b) |   |
|---|---|---|---|
| 1 | Cysteine and/or a salt thereof | at least one compound of formula (II-1) | Oxalic acid |
| 2 | Cysteine and/or a salt thereof | at least one compound of formula (II-2) | Oxalic acid |
| 3 | Cysteine and/or a salt thereof | ethylene carbonate | Oxalic acid |
| 3 | Cysteine and/or a salt thereof | glycerol carbonate | Oxalic acid |
| 4 | Cysteine and/or a salt thereof | propylene carbonate | Oxalic acid |
| 5 | Cysteine and/or a salt thereof | at least one compound of formula (III) | Oxalic acid |
| 6 | Cysteine and/or a salt thereof | glycerol | Oxalic acid |
| 7 | Cysteine and/or a salt thereof | glycerol triacetate | Oxalic acid |
| 8 | Cysteine and/or a salt thereof | at least one compound of formula (IV) | Oxalic acid |

The preferred vehicle suitable for a ready-to-use agent is liquid media such as water or organic solvents different from the components of the inventive active ingredient complex. Preferably the vehicle is a cosmetic vehicle.

Suitable cosmetic vehicles include creams, emulsions, gels or foaming solutions containing surfactants such as shampoos, foams aerosols or other preparations suitable for application to hair in particular. However, it is also conceivable for the ingredients to be in a powdered or tablet form which is dissolved in water before use. The cosmetic vehicles may in particular be aqueous or aqueous-alcoholic.

An aqueous cosmetic vehicle can contains at least 50 wt % water.

Aqueous-alcoholic cosmetic vehicles in the sense of the invention include aqueous solutions containing 3 to 70 wt % of a $C_1$-$C_8$ alcohol different from the compounds of component (b), in particular ethanol and/or isopropanol. Additional alcoholic solvents include methoxybutanol, benzyl alcohol, 2-phenoxyethanol, ethyl diglycol or 1,2-propylene glycol, for example. In another embodiment, the inventive agent additionally contains as a solvent at least one ($C_2$ to $C_6$)-alkyl monoalcohol or a ($C_2$ to $C_6$)-alkanediol, in particular ethanol, isopropanol and/or 1,2-propylene glycol.

The inventive agent preferably has a pH of 1 to 9, in particular 1 to 5, most especially preferably from 1 to 3.

Preferably, the inventive agent additionally contains at least one reductone to enhance the effect. A reductone refers to reductive enediol compounds, which are stabilized by substitution in α-position and are subject to tautomerism. Preferred reductones that may be used according to the invention are ascorbic acid, isoascorbic acid, 2,3-dihydroxy-2-propenedial and 2,3-dihydroxy-2-cyclopentenone.

The reductones are preferably contained in the inventive agent in an amount of 1.0 to 5.0 wt %, based on the weight of the agent.

The following active ingredient combinations are preferred—

|  | Component (a) | Component (b) | Reductone |
|---|---|---|---|
| 1 | Cysteine and/or a salt thereof | at least one compound of formula (II-1) | Ascorbic acid |
| 2 | Cysteine and/or a salt thereof | at least one compound of formula (II-2) | Ascorbic acid |
| 3 | Cysteine and/or a salt thereof | ethylene carbonate | Ascorbic acid |
| 3 | Cysteine and/or a salt thereof | glycerol carbonate | Ascorbic acid |
| 4 | Cysteine and/or a salt thereof | propylene carbonate | Ascorbic acid |
| 5 | Cysteine and/or a salt thereof | at least one compound of formula (III) | Ascorbic acid |
| 6 | Cysteine and/or a salt thereof | glycerol | Ascorbic acid |
| 7 | Cysteine and/or a salt thereof | glycerol triacetate | Ascorbic acid |
| 8 | Cysteine and/or a salt thereof | at least one compound of formula (IV) | Ascorbic acid |
| 9 | Cysteine and/or a salt thereof | at least one compound of formula (II-1) | Isoascorbic acid |
| 10 | Cysteine and/or a salt thereof | at least one compound of formula (II-2) | Isoascorbic acid |
| 11 | Cysteine and/or a salt thereof | ethylene carbonate | Isoascorbic acid |
| 12 | Cysteine and/or a salt thereof | glycerol carbonate | Isoascorbic acid |
| 13 | Cysteine and/or a salt thereof | propylene carbonate | Isoascorbic acid |
| 14 | Cysteine and/or a salt thereof | at least one compound of formula (III) | Isoascorbic acid |
| 15 | Cysteine and/or a salt thereof | glycerol | Isoascorbic acid |
| 16 | Cysteine and/or a salt thereof | glycerol triacetate | Isoascorbic acid |
| 17 | Cysteine and/or a salt thereof | at least one compound of formula (IV) | Isoascorbic acid |

Furthermore, the efficiency of the inventive agents is increased if they additionally contain at least one oxocarboxylic acid. Oxocarboxylic acids are organic compounds which have a carbonyl group in addition to at least one carboxy group and thus are aldehyde acids and/or ketocarboxylic acids. Preferred oxocarboxylic acids include α-oxocarboxylic acids, β-oxocarboxylic acids, γ-oxocarboxylic acids and ω-oxocarboxylic acids. Of these, the compounds of formula (V) and/or their salts are again preferred—

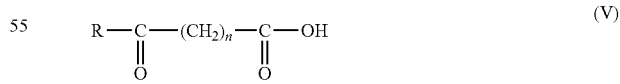

wherein R is a hydrogen atom, a ($C_1$ to $C_6$)-alkyl group, a ($C_1$ to $C_6$)-hydroxyalkyl group, an optionally substituted aryl group, an optionally substituted heteroaryl group, a ($C_2$ to $C_6$)-alkenyl group or a carboxy ($C_1$ to $C_6$)-alkyl group; and n is the number), 1, 2 or 3.

Oxocarboxylic acids are especially preferably chosen from at least one of glyoxalic acid, acetoacetic acid, 3-oxoglutaric acid, 4-oxovaleric acid and pyruvic acid and/or the salts of the aforementioned acids.

The following active ingredient combinations are preferred—

| | Component (a) | Component (b) | Reductone |
|---|---|---|---|
| 1 | Cysteine and/or a salt thereof | at least one compound of formula (II-1) | Glyoxalic acid |
| 2 | Cysteine and/or a salt thereof | at least one compound of formula (II-2) | Glyoxalic acid |
| 3 | Cysteine and/or a salt thereof | ethylene carbonate | Glyoxalic acid |
| 3 | Cysteine and/or a salt thereof | glycerol carbonate | Glyoxalic acid |
| 4 | Cysteine and/or a salt thereof | propylene carbonate | Glyoxalic acid |
| 5 | Cysteine and/or a salt thereof | at least one compound of formula (III) | Glyoxalic acid |
| 6 | Cysteine and/or a salt thereof | glycerol | Glyoxalic acid |
| 7 | Cysteine and/or a salt thereof | glycerol triacetate | Glyoxalic acid |
| 8 | Cysteine and/or a salt thereof | at least one compound of formula (IV) | Glyoxalic acid |
| 9 | Cysteine and/or a salt thereof | at least one compound of formula (II-1) | 3-Oxoglutaric acid |
| 10 | Cysteine and/or a salt thereof | at least one compound of formula (II-2) | 3-Oxoglutaric acid |
| 11 | Cysteine and/or a salt thereof | ethylene carbonate | 3-Oxoglutaric acid |
| 12 | Cysteine and/or a salt thereof | glycerol carbonate | 3-Oxoglutaric acid |
| 13 | Cysteine and/or a salt thereof | propylene carbonate | 3-Oxoglutaric acid |
| 14 | Cysteine and/or a salt thereof | at least one compound of formula (III) | 3-Oxoglutaric acid |
| 15 | Cysteine and/or a salt thereof | glycerol | 3-Oxoglutaric acid |
| 16 | Cysteine and/or a salt thereof | glycerol triacetate | 3-Oxoglutaric acid |
| 17 | Cysteine and/or a salt thereof | at least one compound of formula (IV) | 3-Oxoglutaric acid |

Oxocarboxylic acids are preferably present in the inventive agent in an amount of 1.0 to 5.0 wt %, based on total weight of the agent.

Cosmetic agents used in the inventive method may also contain active ingredients, additives and excipients known for such preparations.

Rewashing with a shampoo is omitted if a vehicle with strong surfactant content is used.

In many cases, the agents contain at least one surfactant, with anionic and zwitterionic, ampholytic, nonionic and cationic surfactants being suitable. However, in many cases it has proven advantageous to select surfactants from anionic, zwitterionic or nonionic surfactants.

Anionic surfactants suitable for use in the cosmetic agents include all anionic surface-active agents suitable for use on the human body. These have a water-solubilizing anionic group (e.g., a carboxylate, sulfate, sulfonate or phosphate group) and a lipophilic alkyl group with approximately 10 to 22 carbon atoms. In addition, glycol or polyglycol ether groups, ester, ether and amide groups, as well as hydroxy groups may also be present in the molecule. Examples of suitable anionic surfactants include, each in the form of the sodium, potassium and ammonium salts as well as the mono-, di- and trialkanolammonium salts with two or three carbon atoms in the alkanol group:

- linear fatty acids with 10 to 22 carbon atoms (soaps),
- ether carboxylic acids of the formula R—O—(CH$_2$—CH$_2$O)$_x$—CH$_2$—COOH, in which R is an alkyl group with 10 to 22 carbon atoms and x=0 or 1 to 16,
- acylsarcosides with 10 to 18 carbon atoms in the acyl group,
- acyltaurides with 10 to 18 carbon atoms in the acyl group,
- acylisethionates with 10 to 18 carbon atoms in the acyl group,
- sulfosuccinic acid mono- and dialkyl esters with 8 to 18 carbon atoms in the alkyl group and sulfosuccinic acid monoalkylpolyoxyethyl esters with 8 to 18 carbon atoms in the alkyl group and 1 to 6 oxyethyl groups,
- linear alkanesulfonates with 12 to 18 carbon atoms,
- linear α-olefinsulfonates with 12 to 18 carbon atoms,
- α-sulfo fatty acid methyl esters of fatty acids with 12 to 18 carbon atoms,
- alkyl sulfates and alkyl polyglycol ether sulfates of the formula R—O(CH$_2$—CH$_2$O)$_x$—SO$_3$H, wherein R is preferably a linear alkyl group with 10 to 18 carbon atoms and x=0 or 1 to 12,
- anionic alkyl oligoglycosides and/or anionic alkenyl oligoglycoside derivatives, selected from alkyl and/or alkenyl oligoglycoside carboxylates, sulfates, phosphates and/or isethionates, which are derived from alkyl and/or alkenyl oligoglycosides of the general formula (VI)—

$$R—O-(G)_p \quad (VI)$$

wherein R is C$_{6-22}$ alkyl or C$_{6-22}$ alkenyl; G is a glycoside unit derived from a sugar with 5 or 6 carbon atoms; and p is a number from 1 to 10, in particular the lauryl glucoside carboxylate obtainable as Plantapon® LGC from Cognis Deutschland,

- mixtures of surface-active hydroxysulfonates according to DE-A-37 25 030,
- sulfated hydroxyalkyl polyethylene and/or hydroxyalkylene propylene glycol ethers according to DE-A-37 23 354,
- sulfonates of unsaturated fatty acids with 12 to 24 carbon atoms and 1 to 6 double bonds according to DE-A-39 26 344, and
- esters of tartaric acid and citric acid with alcohols, which are the addition products of approximately 2-15 molecules of ethylene oxide and/or propylene oxide onto fatty alcohols with 8 to 22 carbon atoms.

Preferred anionic surfactants include alkyl sulfates, alkyl polyglycol ether sulfates and ether carboxylic acids with 10 to 18 carbon atoms in the alkyl group and up to 12 glycol ether groups in the molecule, as well as salts of saturated and unsaturated C$_8$-C$_{22}$ carboxylic acids such as oleic acid, stearic acid, isostearic acid and palmitic acid.

Nonionic surfactants contain as the hydrophilic group a polyol group, a polyalkylene glycol ether group or a combination of polyol and polyglycol ether groups. Such compounds include, for example:

- addition products of 2 to 30 mol ethylene oxide and/or 0 to 5 mol propylene oxide onto linear fatty alcohols with 8 to 22 carbon atoms, onto fatty acids with 12 to 22 carbon atoms and onto alkyl phenols with 8 to 15 carbon atoms in the alkyl group,
- C$_{12}$-C$_{22}$ fatty acid mono- and diesters of addition products of 1 to 30 mol ethylene oxide onto glycerol,
- C$_8$-C$_{22}$ alkyl mono- and oligoglycosides and their ethoxylated analogs, as well as addition products of 5 to 60 mol ethylene oxide onto castor oil and hardened castor oil.

Preferred nonionic surfactants include alkyl polyglycosides of general formula $R^1O$—$(Z)x$. These compounds are characterized by the following parameters.

The alkyl radical $R^1$ contains 6 to 22 carbon atoms and may be either linear or branched. Primary linear radicals and aliphatic radicals with a methyl branching in position 2 are preferred. Such alkyl radicals include 1-octyl, 1-decyl, 1-lauryl, 1-myristyl, 1-cetyl and 1-stearyl. Especially preferred are 1-octyl, 1-decyl, 1-lauryl, 1-myristyl. Compounds with an odd number of carbon atoms in the alkyl chain are predominant when using so-called "oxo alcohols" as the starting materials.

Alkyl polyglycosides that can be used according to the invention may contain, for example, only one certain alkyl radical $R^1$. However, these compounds are usually synthesized by starting with natural fats and oils or mineral oils. In this case, mixtures according to the starting compounds and/or according to the respective workup of these compounds are used as the alkyl radicals R.

Such alkyl polyglycosides, in which $R^1$ consists essentially of $C_8$ and $C_{10}$ alkyl groups, essentially of $C_{12}$ and $C_{14}$ alkyl groups, essentially of $C_8$ and $C_{16}$ alkyl groups or essentially of $C_{12}$ and $C_{16}$ alkyl groups are especially preferred.

Any mono- or oligosaccharides may be used as the sugar building block Z. Sugars with 5 and/or 6 carbon atoms and the corresponding oligosaccharides are usually used. Such sugars include glucose, fructose, galactose, arabinose, ribose, xylose, lyxose, allose, altrose, mannose, gulose, idose, talose and sucrose. Preferred sugar building blocks include glucose, fructose, galactose, arabinose and sucrose, with glucose especially preferred.

Alkyl polyglycosides that may be used according to the invention contain on average 1.1 to 5 sugar units. Alkyl polyglycosides with x values of 1.1 to 1.6 are preferred. Most especially preferred are alkyl glycosides, in which x is 1.1 to 1.4.

In addition to their surfactant action, alkyl glycosides may also be used to improve the fixation of scent components on the hair. Those skilled in the art may preferably use this class of substances as an additional ingredient in the inventive preparations when it is desirable for the effect of the perfume oil on hair to last beyond duration of the hair treatment.

Alkoxylated homologs of the aforementioned alkyl polyglycosides may also be used according to the invention. These homologs may contain on average up to 10 ethylene oxide units and/or propylene oxide units per alkyl glycoside unit.

Zwitteronic surfactants may also be used, in particular as cosurfactants. Zwitteronic surfactants are surface-active compounds having at least one quaternary ammonium group and at least one —$COO^{(-)}$ or $SO_3^{(-)}$ group in the molecule. Particularly suitable zwitteronic surfactants include betaines, such as N-alkyl-N,N-dimethylammonium glycinates (e.g., cocoalklyl dimethylammonium glycinate), N-acylaminopropyl-N,N-dimethyl ammonium glycinates (e.g., cocoacylaminopropyldimethylammonium glycinate) and 2-alkyl-3-carboxylmethyl-3-hydroxyethylimidazolines, each with 8 to 18 carbon atoms in the alkyl or acyl group and cocoacylaminoethyl-hydroxyethyl carboxymethyl glycinate. A preferred zwitterionic surfactant is the fatty acid amide derivative known by the INCI designation cocamidopropyl betaine.

Ampholytic surfactants are also suitable as cosurfactants. Ampholytic surfactants refer to those surface-active compounds which contain, in addition to a $C_8$-$C_{18}$ alkyl or acyl group, at least one free amino group and at least one —COOH or —$SO_3H$ group in the molecule and are suitable for forming internal salts. Examples of suitable ampholytic surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each with approximately 8 to 18 carbon atoms in the alkyl group. Especially preferred ampholytic surfactants include N-cocoalkylaminopropionate, cocoacylaminoethylaminopropionate and $C_{12-18}$ acylsarcosine.

According to the invention, cationic surfactants used are in particular those of quaternary ammonium compounds, ester quats and amidoamines.

Preferred quaternary ammonium compounds include ammonium halides, in particular chlorides and bromides such as alkyltrimethylammonium chlorides, dialkyldimethylammonium chlorides and trialkylmethylammonium chlorides (e.g., cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride), as well as imidazolium compounds known by the INCI designations quaternium-27 and quaternium-83. Long alkyl chains of the surfactants mentioned above preferably have 10 to 18 carbon atoms.

Ester quats are known substances containing at least one ester function as well as at least quaternary ammonium group as a structural element. Preferred ester quats include quaternized ester salts of fatty acids with triethanolamine, quaternized ester salts of fatty acids with diethanol alkylamines and quaternized ester salts of fatty acids with 1,2-dihydroxypropyl dialkylamines. Such products are distributed, for example, under the brand names Stepantex®, Dehyquart® and Armocare®. The products Armocare® VGH-70 and N,N-bis(2-palmitoyloxyethyl)dimethyl-ammonium chloride and Dehyquart® F-75 and Dehyquart® AU-35 are examples of such ester quats.

Alkylamidoamines are usually synthesized by amidation of natural or synthetic fatty acids and fatty acid cuts with dialkylaminoamines. A compound from this substance group especially suitable according to the invention is stearamidopropyl dimethylamine, available commercially under the brand name Tegoamid® S 18.

Other cationic surfactants that can be used according to the invention include quaternized protein hydrolysates.

Cationic silicone oils such as the commercially available products Q2-7224 (manufacturer: Dow Corning; stabilized trimethylsilyl amodimethicone), Dow Corning 929 emulsion (containing a hydroxylamino-modified silicone, also known as amodimethicone) SM-2059 (manufactured by General Electric), SLM-55067 (manufactured by Wacker) and Abil®-Quat 3270 and 3272 (manufactured by Th. Goldschmidt; diquaternary polydimethylsiloxanes, quaternium-80) are also suitable.

An example of a quaternary sugar derivative that may be used as a cationic surfactant is the commercial product Glucquat® 100, known according to INCI nomenclature as a "lauryl methyl gluceth-10 hydroxypropyl dimonium chloride".

Compounds with alkyl groups that are used as surfactants may be uniform substances. However, it is usually preferable to start with native plant or animal raw materials in the production of these substances so that substance mixtures with different alkyl chain lengths are obtained, depending on the particular raw material used.

Products with a "normal" homolog distribution as well as those with a narrow-range homolog distribution may be used as surfactants, which are the addition products of ethylene oxide and/or propylene oxide onto fatty alcohols or derivatives of these addition products. A "normal" homolog distribution refers to mixtures of homologs obtained in the reaction of fatty alcohol and alkylene oxide using alkali metals, alkali metal hydroxides or alkali metal alcoholates as catalysts. However, narrow-range homolog distributions are obtained when hydrotalcites, alkaline earth metal salts of ether carboxylic acids, alkaline earth metal oxides, hydroxide or alcoholates, for example, are used as catalysts. The use of products with a narrow-range homolog distribution may be preferred.

Inventive agents may additionally contain at least one silicone to enhance fiber care without reducing decoloring power. Silicones, when present in the inventive agents, are preferably present in amounts of 0.05 to 5 wt %, preferably 0.2 to 5 wt %, each based on the ready-to-use agent.

Silicones are in particular preferably chosen from at least one representative from the list formed by
  (i) polyalkylsiloxanes, polyarylsiloxanes, polyalkylarylsiloxanes, which are volatile or nonvolatile, linear, branched or cyclic, crosslinked or not crosslinked;
  (ii) polysiloxanes having one or more organofunctional groups in their general structure, chosen from substituted or unsubstituted aminated groups; (per)fluorinated groups; thiol groups; carboxylate groups; hydroxylated groups; alkoxylated groups; acyloxyalkyl groups; amphoteric groups; bisulfite groups; hydroxyacylamino groups; carboxy groups; sulfonic acid groups; and sulfate or thiosulfate groups;
  (iii) linear polysiloxane (A) polyoxyalkylene (B) block copolymers of the (A-B)$_n$ type, wherein n>3;
  (iv) grafted silicone polymers with an organic basic structure not containing silicone, consisting of an organic main chain formed by organic monomers not containing silicone and onto which at least one polysiloxane macromer has been grafted in the chain and optionally on at least one chain end;
  (v) grafted siloxane polymers with a polysiloxane basic structure, onto which organic monomers not containing silicone have been grafted and that have a polysiloxane main chain, onto which at least one macromer not containing silicone has been grafted in the chain and optionally on at least one of its ends, such as the commercial product Abil B 8832 from the company Degussa, distributed under the INCI designation bis-PEG/PPG-20/20 dimethicone; or
  (vi) mixtures thereof.

Especially preferred inventive cosmetic or dermatological preparations are contain at least one silicone of the formula (Si-1)

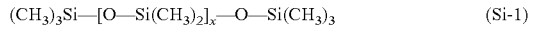

(Si-1)

wherein x is a number from 0 to 100, preferably from 0 to 50, more preferably from 0 to 20, and in particular from 0 to 10.

Cosmetic or dermatological preparations preferred according to the invention contain a silicone of formula (Si-1) above. These silicones are known as dimethicones according to INCI nomenclature. Compounds preferred for use as the silicone of formula (Si-1) within the scope of the invention include—

(CH$_3$)$_3$Si—O—Si(CH$_3$)$_3$
(CH$_3$)$_3$Si—O—(CH$_3$)$_2$Si—O—Si(CH$_3$)$_3$
(CH$_3$)$_3$Si—[O—(CH$_3$)$_2$Si]$_2$—O—Si(CH$_3$)$_3$
(CH$_3$)$_3$Si—[O—(CH$_3$)$_2$Si]$_3$—O—Si(CH$_3$)$_3$
(CH$_3$)$_3$Si—[O—(CH$_3$)$_2$Si]$_4$—O—Si(CH$_3$)$_3$
(CH$_3$)$_3$Si—[O—(CH$_3$)$_2$Si]$_5$—O—Si(CH$_3$)$_3$
(CH$_3$)$_3$Si—[O—(CH$_3$)$_2$Si]$_6$—O—Si(CH$_3$)$_3$
(CH$_3$)$_3$Si—[O—(CH$_3$)$_2$Si]$_7$—O—Si(CH$_3$)$_3$
(CH$_3$)$_3$Si—[O—(CH$_3$)$_2$Si]$_8$—O—Si(CH$_3$)$_3$
(CH$_3$)$_3$Si—[O—(CH$_3$)$_2$Si]$_9$—O—Si(CH$_3$)$_3$
(CH$_3$)$_3$Si—[O—(CH$_3$)$_2$Si]$_{10}$—O—Si(CH$_3$)$_3$
(CH$_3$)$_3$Si—[O—(CH$_3$)$_2$Si]$_{11}$—O—Si(CH$_3$)$_3$
(CH$_3$)$_3$Si—[O—(CH$_3$)$_2$Si]$_{12}$—O—Si(CH$_3$)$_3$
(CH$_3$)$_3$Si—[O—(CH$_3$)$_2$Si]$_{13}$—O—Si(CH$_3$)$_3$
(CH$_3$)$_3$Si—[O—(CH$_3$)$_2$Si]$_{14}$—O—Si(CH$_3$)$_3$
(CH$_3$)$_3$Si—[O—(CH$_3$)$_2$Si]$_{15}$—O—Si(CH$_3$)$_3$
(CH$_3$)$_3$Si—[O—(CH$_3$)$_2$Si]$_{16}$—O—Si(CH$_3$)$_3$
(CH$_3$)$_3$Si—[O—(CH$_3$)$_2$Si]$_{17}$—O—Si(CH$_3$)$_3$
(CH$_3$)$_3$Si—[O—(CH$_3$)$_2$Si]$_{18}$—O—Si(CH$_3$)$_3$
(CH$_3$)$_3$Si—[O—(CH$_3$)$_2$Si]$_{19}$—O—Si(CH$_3$)$_3$
(CH$_3$)$_3$Si[O—(CH$_3$)$_2$Si]$_{20}$—O—Si(CH$_3$)$_3$ wherein (CH$_3$)$_3$Si—O—Si(CH$_3$)$_3$, (CH$_3$)$_3$Si—O—(CH$_3$)$_2$—Si—O—(CH$_3$)$_3$ and/or (CH$_3$)$_3$Si[O—(CH$_3$)$_2$Si]$_2$—O—Si(CH$_3$)$_3$ are especially preferred.

Mixtures of the aforementioned silicones may also be contained in the preferred inventive agents.

Preferred silicones for use according to the invention have viscosities of 0.2 to 2 mm$^2$ s$^{-1}$ at 20° C., and silicones with viscosities of 0.5 to 1 mm$^2$ s$^{-1}$ are especially preferred.

Especially preferred inventive agents contain one or more amino-functional silicones. Such silicones can be described by formula (Si-2)

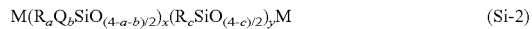

(Si-2)

wherein R is a hydrocarbon or a hydrocarbon residue with 1 to approximately 6 carbon atoms; Q is a polar radical of the general formula R$^1$HZ in which R$^1$ is a divalent linking group bound to hydrogen and to the radical Z, comprised of carbon and hydrogen atoms, carbon, hydrogen and oxygen atoms, or carbon, hydrogen and nitrogen atoms, and Z is an organic amino-functional radical containing at least one amino-functional group; a is a value in the range of approximately 0 to approximately 2; b is a value in the range of approximately 1 to approximately 3; a+b is less than or equal to 3; c is a number in the range from approximately 1 to approximately 3; x is a number in the range from 1 to approximately 2000, preferably from approximately 3 to approximately 50, and most preferably from approximately 3 to approximately 25; and y is a number in the range from approximately 20 to approximately 10,000, preferably from approximately 125 to approximately 10,000, and most preferably from approximately 150 to approximately 1000, and M is a suitable silicone terminal group, as known in the prior art, preferably trimethylsiloxy.

Nonrestrictive examples of radicals represented by R in the formula (SI-2) include alkyl radicals such as methyl, ethyl, propyl, isopropyl, butyl, isobutyl, amyl, isoamyl, hexyl, isohexyl and the like; alkenyl radicals such as vinyl, halovinyl, alkylvinyl, allyl, haloallyl, alkylallyl; cycloalkyl radicals such as cyclobutyl, cyclopentyl, cyclohexyl and the like; phenyl radicals, benzyl radicals, halohydrocarbon radicals such as 3-chloropropyl, 4-bromobutyl, 3,3,3-trifluoropropyl, chlorocyclohexyl, bromophenyl, chlorophenyl and the like as well as sulfur-containing radicals, such as mercaptoethyl, mercaptopropyl, mercaptohexyl, mercaptophenyl and the like. R is preferably an alkyl radical containing 1 to approximately 6 carbon atoms, and R is most preferably methyl. Examples of R$^1$ include methylene, ethylene, propylene, hexamethylene, decamethylene, —CH$_2$CH(CH$_3$)CH$_2$—, phenylene, naphthylene, —CH$_2$CH$_2$SCH$_2$CH$_2$—, —CH$_2$CH$_2$OCH$_2$—, —OCH$_2$CH$_2$—, —OCH$_2$CH$_2$CH$_2$—, —CH$_2$CH(CH$_3$)C(O)OCH$_2$—, (CH$_2$)$_3$CC(O)OCH$_2$CH$_2$—, —C$_6$H$_4$C$_6$H$_4$—, —C$_6$H$_4$—CH$_2$C$_6$H$_4$— and —(CH$_2$)$_3$C(O)SCH$_2$CH$_2$—.

Z in formula (Si-2) is an organic amino-functional radical containing at least one functional amino group. One possible formula for Z is —NH(CH$_2$)$_z$NH$_2$, in which z is an integer greater than or equal to 1. Another possible formula for Z is —NH(CH$_2$)$_z$(CH$_2$)$_{zz}$NH, in which both z and zz are independently an integer greater than or equal to 1, where this structure includes diamino ring structures such as piperazinyl. Z is most preferably an —NHCH$_2$CH$_2$NH$_2$ radical. Another possible formula for Z is —N(CH$_2$)(CH$_2$)$_{zz}$NX$_2$ or —NX$_2$, wherein each X is chosen independently of X$_2$ from hydrogen and alkyl groups with 1 to 12 carbon atoms, and zz is 0.

Q according to formula (Si-2) is most preferably a polar amino-functional radical of the formula —CH$_2$CH$_2$CH$_2$NHCH$_2$CH$_2$NH$_2$.

In the formula (Si-2), a is a value in the range of 0 to 2, b is a value in the range of 2 to 3, a+b is less than or equal to 3, and c is a number in the range of 1 to 3. The molar ratio of R$_a$Q$_b$SiO$_{(4-a-b)/2}$ units to R$_c$SiO$_{(4-c)/2}$ units in formula (Si-2) is in the range of approximately 1:2 to 1:65, preferably approximately 1:5 to approximately 1:65, and most preferably approximately 1:15 to approximately 1:20. If one or more silicones of the above formula (Si-2) are used, then the various variable substituents in the above formula are different in the various silicone components present in the silicone mixture.

Preferred inventive cosmetic or dermatological preparations contain an amino-functional silicone of the formula (Si-3)

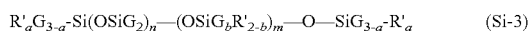

(Si-3)

wherein G is H, a phenyl group, —OH, —O—CH$_3$, —CH$_3$, —O—CH$_2$CH$_3$, —CH$_2$CH$_3$, —O—CH$_2$CH$_2$CH$_3$, —CH$_2$CH$_2$CH$_3$, —O—H(CH$_3$)$_2$, —CH(CH$_3$)$_2$, —O—CH$_2$CH$_2$CH$_2$CH$_3$, —CH$_2$CH$_2$CH$_2$CH$_3$, —O—CH$_2$CH(CH$_3$)$_2$, —CH$_2$CH(CH$_3$)$_2$, —O—CH(CH$_3$)CH$_2$CH$_3$, —CH(CH$_3$)CH$_2$CH$_3$, —O—C(CH$_3$)$_3$, —C(CH$_3$)$_3$; a is a number from 0 to 3, in particular 0; b is for a number from 0 to 1 in particular 1; m and n are numbers, the sum of which (m+n) is from 1 to 2000, preferably from 50 to 150, in which n preferably assumes values from 0 to 1999 and in particular from 49 to 149, and m preferably assumes values from 1 to 2000, in particular from 1 to 10; R' is a monovalent radical chosen from -Q-N(R")—CH$_2$—CH$_2$—N(R")$_2$
-Q-N(R")$_2$
-Q-N$^+$(R")$_3$A$^-$
-Q-N$^+$H(R")$_2$A$^-$
-Q-N$^+$H$_2$(R")A$^-$
-Q-N(R")—CH$_2$—CH$_2$—N$^+$R"H$_2$A$^-$, whereis each Q is a chemical bond, —CH$_2$—, —CH$_2$—CH$_2$—, —CH$_2$—CH$_2$—CH$_2$—, —C(CH$_3$)$_2$—, —CH$_2$—CH$_2$—CH$_2$—CH$_2$—, —CH$_2$C(CH$_3$)$_2$—, or —CH(—CH$_3$)CH$_2$CH$_2$—; R" is the same or different radicals from —H, -phenyl, -benzyl, —CH$_2$—CH(CH$_3$)Ph, C$_{1-20}$-alkyl radicals, preferably —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, and A is an anion preferably chosen from chloride, bromide, iodide or methosulfate.

Suitable according to the invention are cationic silicone oils such as the commercially available Dow Corning 929 emulsion (containing a hydroxylamino-modified silicone, which is referred to as amodimethicone), DC2-2078 (manufacturer: Dow Corning, INCI designation aminopropyl phenyl trimethicone), DC5-7113 (manufacturer: Dow Corning, INCI designation: silicone quatemium-16), SM-2059 (manufacturer: General Electric), SLM-55067 (manufacturer Wacker) and Abil®-Quat 3270 and 3272 (manufacturer: Th. Goldschmidt; diquaternary polydimethylsiloxane, quatemium-80).

Especially preferred inventive agents contain at least one amino-functional silicone of the formula (Si3-a)—

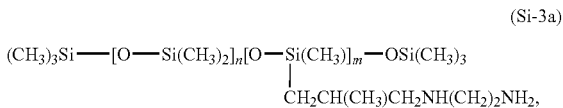

(Si-3a)

wherein m and n are numbers, the sum of which (m+n) is from 1 to 2000, preferably from 50 to 150, where n preferably assumes values from 0 to 1999, and in particular from 49 to 149, and m preferably assumes values from 1 to 2000, in particular from 1 to 10.

These silicones are known as trimethylsilylamodimethicones according to the INCI Declaration and are available under the designation Q2-7224 (manufacturer: Dow Corning; a stabilized trimethylsilyl amodimethicone).

Inventive agents containing at least one amino-functional silicone of the formula (Si-3b) are especially preferred:

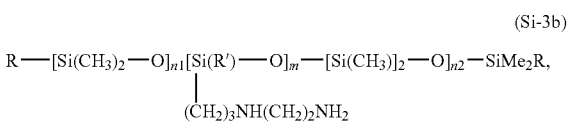

(Si-3b)

wherein R is —OH, a (optionally ethoxylated and/or propoxylated) (C$_1$ to C$_{20}$)-alkoxy group or a —CH$_3$ group; R' is —OH, a (C$_1$ to C$_{20}$)-alkoxy group or a —CH$_3$ group, and m, n1 and n2 are numbers, the sum of which (m+n1+n2) is from 1 to 2000, preferably from 50 to 150, where the sum (n1+n2) preferably assumes values from 0 to 1999, and in particular from 49 to 149, and m preferably assumes values from 1 to 2000, in particular from 1 to 10.

According to the INCI Declaration, these silicones are known as amodimethicones and/or as functionalized amodimethicones, such as bis(C13-15 alkoxy) PG amodimethicone (available from Dow Corning, for example, as the commercial product DC 8500), trideceth-9 PG-amodimethicone (available from Clariant, for example, as the commercial product Silcare Silicone SEA).

Regardless of which amino-functional silicones are used, inventive cosmetic or dermatological preparations containing an amino-functional silicone whose amine number is above 0.25 meq/g, preferably above 0.3 meq/g and in particular above 0.4 meq/g are preferred. The amine number stands for milliequivalents of amine per gram of the amino-functional silicone. It may also be determined by titration and may be given in units of mg KOH/g.

Preferred cosmetic or dermatological preparations according to the invention contain 0.01 to 10 wt %, preferably 0.1 to 8 wt %, especially preferably 0.25 to 7.5 wt % and in particular 0.5 to 5 wt % amino-functional silicone(s).

Cyclic dimethicones, also known as cyclomethicones according to INCI, may be used preferentially according to the invention. Inventive cosmetic or dermatological preparations containing at least one silicone of the formula (Si-4) are preferred here—

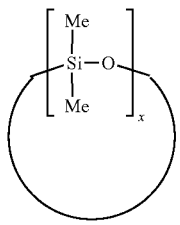
(Si-4)

where x is a number from 0 to 200, preferably from 0 to 10, more preferably from 0 to 7, and in particular 0, 1, 2, 3, 4, 5 or 6.

The silicones described above have a backbone composed of Si—O—Si units. These Si—O—Si units may naturally also be interrupted by carbon chains. Corresponding molecules are accessible by chain-extending reactions and are preferably used in the form of silicone-in-water emulsions.

Silicone-in-water emulsions that may be used according to the invention can be synthesized by known methods, such as those disclosed in U.S. Pat. No. 5,998,537 and EP 0 874 017 A1.

In summary, this synthesis method includes the emulsifying mixture of components, one of which contains at least one polysiloxane, the other of which contains at least one organosilicone material that reacts with the polysiloxane in a chain-extending reaction, at least one metal-ion-containing catalyst being present for the chain-extending reaction, and at least one surfactant and water.

Chain-extending reactions with polysiloxanes are known and may include, for example, hydrosilylation, in which an Si—H group reacts with an aliphatically unsaturated group in the presence of a platinum/rhodium catalyst to form polysiloxanes with a few Si—(C)$_p$—Si bonds (p=1-6), wherein the polysiloxanes are also referred to as polysiloxane-polysilalkylene copolymers.

The chain-extending reaction may also include the reaction of an Si—OH group (for example, a hydroxy-terminated polysiloxane) with an alkoxy group (for example, alkoxysilanes, silicates or alkoxysiloxanes) in the presence of a catalyst containing metal to form polysiloxanes.

The polysiloxanes used in the chain-extending reaction include a substantially linear polymer of the following structure:

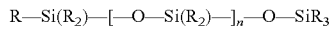
R—Si(R$_2$)—[—O—Si(R$_2$)—]$_n$—O—SiR$_3$

In this structure, each R is independently a hydrocarbon radical with up to 20 carbon atoms, preferably with 1 to 6 carbon atoms, such as an alkyl group (e.g., methyl, ethyl, propyl or butyl), an aryl group (e.g., phenyl) or the group required for the chain-extending reaction ("reactive group," e.g., Si-bound hydrogen atoms, aliphatically unsaturated groups such as vinyl, allyl or hexenyl, hydroxyl; alkoxy such as methoxy, ethoxy or propoxy, alkoxyalkoxy, acetoxy, amino, etc.), with the proviso that, on average, one to two reactive groups are present per polymer, and n is a positive number >1. A plurality of the reactive groups, especially preferably >90%, and in particular >98% are bound to the terminal Si atoms in the siloxane. Preferably n are numbers describing polysiloxanes having viscosities between 1 and 1,000,000 mm$^2$/s, especially preferably viscosities between 1000 and 100,000 mm$^2$/s.

The polysiloxanes may be branched to a slight degree (e.g., <2 mol % of the siloxane units), but the polymers are substantially linear, especially preferably completely linear. Furthermore, the substituents R may in turn be substituted, for example, with N-containing groups (e.g., amino groups), epoxy groups, S-containing groups, Si-containing groups, O-containing groups, etc. At least 80% of the R radicals are preferably alkyl radicals, especially preferably methyl groups.

The organosilicone material which reacts with the polysiloxane in the chain-extending reaction may be either a second polysiloxane or a molecule that acts as a chain extender. If the organosiloxane material is a polysiloxane, it has the general structure mentioned above. In these cases, a polysiloxane will have (at least) one reactive group in the reaction, and a second polysiloxane will have (at least) one second reactive group, which reacts with the first.

If the organosiloxane material comprises a chain-extending agent, this can be a material such as a silane, a siloxane (for example, disiloxane or trisiloxane) or a silazane. For example, a composition comprising a polysiloxane according to the general structure described above having at least one Si—OH group may be chain-extended by reacting it with an alkoxysilane (for example, a dialkoxysilane or trialkoxysilane) in the presence of catalysts containing tin or titanium.

Metal-containing catalysts in the chain-extending reaction are usually specific for a certain reaction. Such catalysts are known in the prior art and contain, for example, metals such as platinum, rhodium, tin, titanium, copper, lead, etc. In a preferred chain-extending reaction, a polysiloxane is reacted with at least one aliphatically unsaturated group, preferably a terminal group, with an organosilicone material in the presence of a hydrosilylation catalyst; this is a siloxane or polysiloxane having at least one (preferably terminal) Si—H group. The polysiloxane has at least one aliphatically unsaturated group and conforms to the general formula given above, in which R and n have the meanings defined above, on the average between one and two R groups having one aliphatically unsaturated group per polymer. Representative aliphatically unsaturated groups include, for example, vinyl, allyl, hexenyl and cyclohexenyl or a R$^2$CH═CHR$^3$ group, in which R$^2$ stands for a divalent aliphatic chain bound to the silicon, and R$^3$ stands for a hydrogen atom or an alkyl group. The organosilicone material having at least one Si—H group preferably has the structure given above, in which R and n are defined as above, and in which, on the average, between one and two R groups denote a hydrogen and n is zero or a positive integer.

This material may be a polymer or a low-molecular material such as a siloxane (for example, a disiloxane or a trisiloxane).

The polysiloxane having at least one aliphatically unsaturated group and the organosilicone material having at least one Si—H group react in the presence of a hydrosilylation catalyst. Such catalysts are known in the prior art and comprise, for example, materials containing platinum and rhodium. The catalyst may assume any known form, for example, platinum or rhodium applied to carrier materials (such as silica gel or activated carbon) or other suitable compounds such as platinum chloride, salts of platinic or chloroplatinic acids. Chloroplatinic acid, either as the commercially available hexahydrate or in anhydrous form, is a catalyst that is preferred because of its good dispersibility in organosilicone systems and the minor color change.

With another preferred chain-extending reaction, a polysiloxane having at least one Si—OH group, preferably a terminal group, is reacted with an organosilicone material having at least one alkoxy group, preferably a siloxane having at least one Si—OR group or an alkoxysilane having at least two alkoxy groups. The catalyst here is again a metal-containing catalyst.

There are many catalysts known in the literature for the reaction of an Si—OH group with an Si—OR group, for example, organometal compounds such as organotin salts, titanates or titanium chelates and/or complexes. Examples include tin octoate, dibutyltin dilaurate, dibutyltin diacetate, dimethyltin dineodecanoate, dibutyltin dimethoxide, isobutyltin triceroate, dimethyltin dibutyrate, dineodecanoate, triethyltin tartrate, tin oleate, tin naphthenate, tin butyrate, tin acetate, tin benzoate, tin sebacate, tin succinate, tetrabutyl titanate, tetraisopropyl titanate, tetraphenyl titanate, tetraoctadecyl titanate, titanium naphthenate, ethyltriethanolamine titanate, titanium diisopropyl diethyl acetoacetate, titanium diisopropoxy diacetyl acetonate and titanium tetraalkoxides, in which the alkoxide is butoxy or propoxy.

Agents also preferred according to the invention contain at least one silicone of the formula (Si-5)

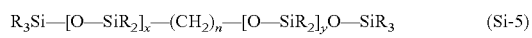   (Si-5)

wherein R is the same or different radicals chosen from —H, -phenyl, -benzyl, —$CH_2$—$CH(CH_3)$Ph, $C_{1-20}$-alkyl radicals, preferably —$CH_3$, —$CH_2CH_3$, —$CH_2CH_2CH_3$, —CH($CH_3$)$_2$, —$CH_2CH_2CH_2H_3$, —$CH_2CH(CH_3)_2$, —$CH(CH_3)CH_2CH_3$, —$C(CH_3)_3$, x and/or y stand for a number from 0 to 200, preferably from 0 to 10, more preferably from 0 to 7, and in particular 0, 1, 2, 3, 4, 5 or 6, and n stands for a number from 0 to 10, preferably from 1 to 8 and in particular 2, 3, 4, 5, 6.

The silicones are preferably water-soluble. Preferred agents according to the invention containing a silicone are those wherein the silicone is water soluble.

Corresponding hydrophilic silicones are chosen from compounds of the formulas (Si-6) and/or (Si-7), for example. Preferred water-soluble surfactants based on silicone are selected in particular from the group of dimethicone copolyols, which are preferably alkoxylated, in particular polyethoxylated or polypropoxylated.

Dimethicone copolyols are preferably polyoxyalkylene-modified dimethylpolysiloxanes of the general formula (Si-6) or (Si-7)—

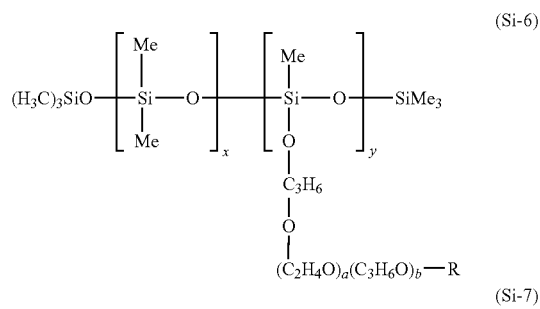

wherein
R is a hydrogen atom, an alkyl group with 1 to 12 carbon atoms, an alkoxy group with 1 to 12 carbon atoms or a hydroxy group,
R' and R" are alkyl groups having 1 to 12 carbon atoms,
x is an integer from 1 to 100, preferably from 20 to 30,
y is an integer from 1 to 20, preferably from 2 to 10, and
a and b are integers from 0 to 50, preferably form 10 to 30.

Especially preferred dimethicone copolyols in the sense of the invention include products distributed commercially under the brand names SILWET (Union Carbide Corporation) and Dow Corning (Dow).

Especially preferred dimethicone copolyols according to the invention are Dow Corning 190 and Dow Corning 193 (Dow).

In addition, inventive agent preferably contains at least one cationic polymer for conditioning hair. Inventive agents containing such a polymer do not show any decline in efficiency of the decoloring power, but instead have a slightly enhanced effect.

Cationic polymers are understood according to the invention to be polymers having a "temporarily" or "permanently" cationic group in the main chain and/or side chain. According to the invention, "permanently cationic" refers to polymers having a cationic group regardless of the pH of the agent. These are usually polymers containing a quaternary nitrogen atom, e.g., in the form of an ammonium group. Quaternary ammonium groups are preferred cationic groups. In particular, polymers in which the quaternary ammonium group is bound by a $C_{1-4}$ hydrocarbon group to a polymer main chain composed of acrylic acid, methacrylic acid or derivatives thereof have proven to be especially suitable.

Especially preferred cationic polymers are homopolymers of the general formula (G1-I)

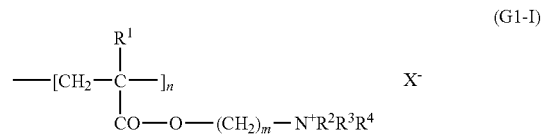   (G1-I)

in which $R^1$=H or $CH_3$, $R^2$, $R^3$ and $R^4$ are independently chosen from $C_{1-4}$ alkyl, alkenyl or hydroxyalkyl groups, m=1, 2, 3 or 4, n is a natural number and $X^-$ is a physiologically tolerable organic or inorganic anion, as well as copolymers consisting essentially of monomer units defined in formula (G1-I) as well as nonionic monomer units. Within the scope of these polymers, those for which at least one of the following conditions apply are especially preferred according to the invention:
$R^1$ is a methyl group,
$R^2$, $R^3$ and $R^4$ are for methyl groups, and
m has a value of 2.

Physiologically tolerable counterions $X^-$ can be, for example, halide ions, sulfate ions, phosphate ions, and methosulfate ions, as well as organic ions such as lactate, citrate, tartrate and acetate ions. Halide ions, in particular chloride are preferred.

An especially suitable homopolymer is poly(methacryloyloxyethyl trimethyl ammonium chloride), which is crosslinked, if desired, and has the INCI designation polyquaternium-37. If desired, crosslinking may be accomplished with the help of olefinically polyunsaturated compounds, for example, divinylbenzene, tetraallyloxyethane, methylene bisacrylamide, diallyl ether, polyallylpolyglyceryl ether or ally ethers of sugars or sugar derivatives, such as erythritol, pentaerythritol, arabitol, mannitol, sorbitol, sucrose or glucose. Methylene bisacrylamide is a preferred crosslinking agent.

The homopolymer is preferably used in the form of a nonaqueous polymer dispersion having a polymer content of no less than 30 wt %. Such polymer dispersions are commercially available under the designations Salcare® SC 95 (approximately 50% polymer content, additional components: mineral oil (INCI designation: mineral oil) and tridecylpolyoxypropylene polyoxyethylene ether (INCI designation PPG-1 trideceth-6)) and Salcare® SC 96 (approximately 50% polymer content, additional components: mixture of diesters of propylene glycol with a mixture of caprylic acid and capric acid (INCI designation: propylene glycol dicaprylate/dicaprate) and tridecylpolyoxy-propylene polyoxyethylene ether (INCI designation: PPG-1 trideceth-6)).

Copolymers with monomer units according to formula (G1-I) preferably contain as nonionic monomer units acrylamide, methacrylamide, acrylic acid $C_{1-4}$-alkyl esters and methacrylic acid $C_{1-4}$-alkyl esters. Of these nonionic monomers, acrylamide is especially preferred. These copolymers may also be crosslinked as described above for the homopolymers. A preferred copolymer according to the invention is crosslinked acrylamide methacryloyloxyethyltrimethylammonium chloride copolymer. Such copolymers in which the monomers are present in a weight ratio of approximately 20:80 are available commercially as an approximately 50% nonaqueous polymer dispersion under the designation Salcare SC 92.

Additional preferred cationic polymers include, for example—
- quaternized cellulose derivatives, such as those available commercially under the designations Celquat® and Polymer JR®. The compounds Celquat® H 100, Celquat® L 200 and Polymer JR® 400 are preferred quaternized cellulose derivatives,
- cationic alkyl polyglycosides according to DE-PS 44 13 686
- cationized honey, for example, the commercial product Honeyquat® 50,
- cationic guar derivatives, such as the products distributed under the designations Cosmedia® guar and Jaguar® in particular,
- polysiloxanes with quaternary groups such as the commercially available products Q2-7224 (manufacturer: Dow Corning; a stabilized trimethylsilyl amodimethicone), Dow Corning 929 emulsion (containing a hydroxylamino-modified silicone, which is also known as amodimethicone), SM-2059 (manufacturer: General Electric), SLM-55067 (manufacturer: Wacker) and Abil®-Quat 3270 and 3272 (manufacturer: Th. Goldschmidt), diquaternary polydimethylsiloxanes, quaternium-80),
- polymeric dimethyldiallylammonium salts and their copolymers with esters and amides of acrylic acid and methacrylic acid. The products available commercially under the designations Merquat® 100 (polydimethyldiallyl ammonium chloride)) and Merquat® 550 (dimethyldiallylammonium chloride-acrylamide copolymer) are examples of such cationic polymers,
- copolymers of vinylpyrrolidone with quaternized derivatives of dialkylaminoalkyl acrylate and methacrylate, such as vinylpyrrolidone dimethylaminoethyl methacrylate copolymers quaternized with diethyl sulfate. Such compounds are available commercially under the designations Gafquat® 734 and Gafquat® 755,
- vinylpyrrolidone-vinylimidazolium methochloride copolymers, such as those available under the designations Luviquat® FC 370, FC 550, FC 905 and HM 552,
- quaternized polyvinyl alcohol,
- as well as polymers having quaternary nitrogen atoms in the polymer main chain, known by the designations polyquaternium-2, polyquaternium-17, polyquaternium-18 and polyquaternium-27.

Polymers known by the designations polyquaternium-24 (commercial product, e.g., Quatrisoft® LM 200) may also be used as cationic polymers. The copolymers of vinylpyrrolidone, such as the commercial products Copolymer 845 (manufacturer: ISP), Gaffix® VC 713 (manufacturer: ISP), Gafquat® ASCP 1011, Gafquat® HS 110, Luviquat® 8155 and Luviquat® MS 370, may also be used.

Other inventive cationic polymers include the so-called "temporarily cationic" polymers. These polymers usually contain an amino group, which is present as a quaternary ammonium group and is thus cationic at certain pH levels. For example, chitosan and its derivatives, such as those freely available commercially under the brand names Hydagen® CMF, Hydagen® HCMF, Kytamer® PC and Chitolam® NB/101, are preferred.

Cationic polymers preferred according to the invention include cationic cellulose derivatives and chitosan and its derivatives, in particular, the commercial products Polymer® JR 400, Hydagen® HCMF and Kytamer® PC, cationic guar derivatives, cationic honey derivatives, in particular, the commercial product Honeyquat® 50, cationic alkyl polyglycosides according to DE-PS 44 13 686 and polyquaternium-37 polymers.

In addition, cationized protein hydrolysates can also be counted with the cationic polymers. Basic protein hydrolysate can originate from an animal source (e.g., from collagen, milk or keratin), from a plant source (e.g., from wheat, corn, rice, potatoes, soy or almonds), from marine life forms (e.g., from fish collagen or algae), or from protein hydrolysates obtained by biotechnology. Protein hydrolysates formed on the basis of the inventive cationic derivatives can be extracted from the corresponding proteins by chemical hydrolysis, in particular, alkaline or acidic hydrolysis, by enzymatic hydrolysis and/or a combination of the two types of hydrolysis. As a rule, hydrolysis of proteins yields a protein hydrolysate having a molecular weight distribution from approximately 100 Daltons up to several thousand Daltons. Such cationic protein hydrolysates, whose basic protein content has a molecular weight of 100 to 25,000 Daltons, preferably 250 to 5000 Daltons, are preferred. In addition, cationic protein hydrolysates are also understood to include quaternized amino acids and mixtures thereof. Quaternization of the protein hydrolysates or amino acids is often performed by quaternary ammonium salts, e.g., N,N-dimethyl-N-(n-alkyl)-N-(2-hydroxy-3-chloro-n-propyl)ammonium halides. In addition, the cationic protein hydrolysates may also be further derivatized. Typical examples of inventive cationic protein hydrolysates and derivatives include commercially available products mentioned under the following INCI designations in the *International Cosmetic Ingredient Dictionary and Handbook* ($7^{th}$ edition 1997, The Cosmetic, Toiletry, and Fragrance Association, 1101 $17^{th}$ Street, N.W., Suite 300, Washington, D.C. 20036-4702): cocodimonium hydroxypropyl hydrolyzed collagen, coco-dimonium hydroxypropyl hydrolyzed casein, cocodimonium hydroxypropyl hydrolyzed collagen, cocodimonium hydroxypropyl hydrolyzed hair keratin, cocodimonium hydroxypropyl hydrolyzed keratin, cocodimonium hydroxypropyl hydrolyzed rice protein, cocodimonium hydroxypropyl hydrolyzed soy protein, cocodimonium hydroxypropyl hydrolyzed wheat protein, hydroxypropyl arginine lauryl/myristyl ether HCl, hydroxypropyltrimonium gelatin, hydroxypropyltrimonium hydrolyzed casein, hydroxypropyltrimonium hydrolyzed collagen, hydroxypropyltrimonium hydrolyzed conchiolin protein, hydroxypropyltrimonium hydrolyzed keratin, hydroxypropyltrimonium hydrolyzed rice bran protein, hydroxypropyltrimonium hydrolyzed soy protein, hydroxypropyl hydrolyzed vegetable protein, hydroxypropyltrimonium hydrolyzed wheat protein, hydroxypropyltrimonium hydrolyzed wheat protein/siloxysilicate, laurdimonium hydroxypropyl hydrolyzed soy protein, laurdimonium hydroxypropyl hydrolyzed wheat protein, laurdimonium hydroxypropyl hydrolyzed wheat protein/siloxysilicate, lauryldimonium hydroxypropyl hydrolyzed casein, lauryldimonium hydroxypropyl hydrolyzed collagen, lauryldimonium hydroxypropyl hydrolyzed keratin, lauryldimonium hydroxypropyl hydrolyzed soy protein, steardimonium hydroxypropyl hydrolyzed casein, steardimonium hydroxypropyl hydrolyzed collagen, steardimonium hydroxypropyl hydrolyzed keratin, steardimonium hydroxypropyl hydrolyzed rice protein, steardimonium hydroxypropyl hydrolyzed soy protein, steardimonium hydroxypropyl hydrolyzed vegetable protein, steardimonium hydroxypropyl hydrolyzed wheat protein, steardimonium hydroxypropyl hydrolyzed collagen, quaternium-76 hydrolyzed collagen, quaternium-79 hydrolyzed collagen, quaternium-79 hydrolyzed keratin, quaternium-79 hydrolyzed milk protein, quaternium-79 hydrolyzed soy protein, quaternium-79 hydrolyzed wheat protein.

Most especially preferred are cationic protein hydrolysates and derivatives based on plant sources.

Amphoteric polymers preferred for use include polymer products composed essentially of
(a) monomers with quaternary ammonium groups of the general formula (M-I)

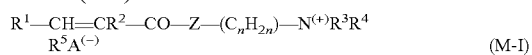
(M-I)

wherein $R^1$ and $R^2$ are independently hydrogen or a methyl group, and $R^3$, $R^4$ and $R^5$ are independently alkyl groups with 1 to 4 carbon atoms, Z is an NH group or an oxygen atom, n is an integer from 2 to 5, and $A^{(-)}$ is the anion of an organic or inorganic acid, and
(b) monomeric carboxylic acids of the general formula (M-II)

(M-II)

in which $R^6$ and $R^7$ are independently hydrogen or methyl groups.

These compounds may be used according to the invention either directly or in salt form, obtained by neutralization of the polymer products (e.g., with an alkali hydroxide). With regard to details of the synthesis of these polymer products, reference is made to unexamined German Patent 39 29 973. Most especially preferred are polymer products in which monomers of the type (a) are used, where $R^3$, $R^4$ and $R^5$ are methyl groups, Z is an NH group, and $A^{(-)}$ is a halide, methoxysulfate or ethoxysulfate ion; acrylamidopropyl trimethylammonium chloride is an especially preferred monomer (a). Acrylic acid is preferably used as monomer (b) for the aforementioned polymer products.

The inventive color-changing agents preferably contain cationic polymers in an amount of 0.01 to 5 wt %, in particular in an amount of 0.1 to 2 wt %, each based on total application preparation.

The inventive agent is preferably especially effective when it has a viscosity of 500 to 30,000 mPa·s, in particular from 1000 to 10,000 mPa·s (each measured with a Brookfield DV-II+, spindle 4, 20 rpm at 20° C.).

Thus, preferably at least one thickening agent is added to the inventive agent. Thickening polymers are preferably suitable for thickening the inventive agents. In aqueous phases, their viscosity-increasing function is based on their solubility in water or their hydrophilic nature. The polymers used for thickening according to the invention are used both in surfactant systems and in emulsion systems.

Polymeric thickeners which have a thickening effect at an acidic pH, preferably in the preferred viscosity range stated above, are preferred for use here.

Especially preferably suitable thickening polymers include xanthan gum and/or cellulose and/or derivatives of cellulose, in particular cellulose ethers.

Cellulose ethers preferred for use as the thickening polymer contain structural elements of the formula Cell-1

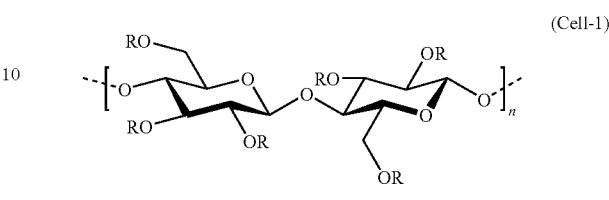
(Cell-1)

wherein R independently of its position in the structural element, is a hydrogen atom, a methyl group, an ethyl group, a propyl group, an octyl group, a dodecyl group, a hexadecyl group, a —$CH_2CH_2$—(O—$CH_2CH_2$)$_y$—OH radical; where y≥0, or a —$CH_2CHMe$—(O—$CH_2CHMe$)$_z$-OH radical; where z≥0; n is an integer from 300 to 15,000, with the proviso that at least one R radical is different from a hydrogen atom.

It is preferable if at least one R radical according to the formula (Cell-1) is a —$CH_2CH_2$—(O—$CH_2CH_2$)$_y$—OH radical, where y≥0, or a —$CH_2CHMe$—(O—$CH_2CHMe$)$_z$-OH radical, where z≥0.

To adjust the viscosity, the inventive agents most especially preferably contain at least one thickening polymer chosen from hydroxyethyl cellulose (e.g., Natrosol® 250 HR from Hercules), hydroxypropyl cellulose (e.g., Klucel PR® from Hercules), methylhydroxyethyl cellulose (e.g., Culminal® MHEC 8000 from Hercules), methylhydroxypropyl cellulose (e.g., Benecel® MP 943 R from Hercules) and hexadecylhydroxyethyl cellulose (e.g., Natrosol® plus grade 330 PA from Hercules).

Keratin-containing fibers to be decolored are preferably dyed with oxidative dyes and/or substantive dyes, as representatives of the synthetic dyes.

In principle, the following developer components can serve to dye the developer components used for decoloring keratin-containing fibers.

It may be preferable according to the invention to use a p-phenylenediamine derivative or one of its physiologically tolerable salts as the developer component. Especially preferred are p-phenylenediamine derivatives of the formula (E1)—

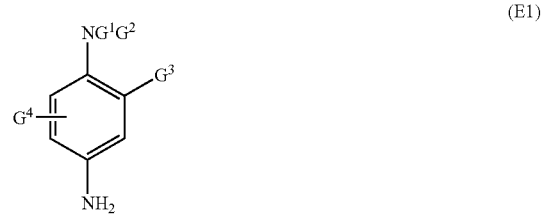
(E1)

wherein $G^1$ is a hydrogen atom, a ($C_1$ to $C_4$)-alkyl radical, a ($C_1$ to $C_4$)-monohydroxyalkyl radical, a ($C_2$ to $C_4$)-polyhydroxyalkyl radical, a ($C_1$ to $C_4$)-alkoxy-($C_1$ to $C_4$)-alkyl radical, a 4'-aminophenyl radical or a ($C_1$ to $C_4$)-alkyl radical substituted with a nitrogenous group, a phenyl or a 4'-aminophenyl radical; $G^2$ is a hydrogen atom, a ($C_1$ to $C_4$)-alkyl radical, a ($C_1$ to $C_4$)-monohydroxyalkyl radical, a ($C_2$ to $C_4$)-polyhydroxyalkyl radical, a ($C_1$ to $C_4$)-alkoxy ($C_1$ to $C_4$)- alkyl radical or a ($C_1$ to $C_4$)-alkyl radical substituted with a nitrogenous group; $G^3$ is a hydrogen atom, a halogen atom, such as a chlorine, bromine, iodine or fluorine atom, a ($C_1$ to $C_4$)-alkyl radical, a ($C_1$ to $C_4$)-monohydroxyalkyl radical, a ($C_2$ to $C_4$)-polyhydroxyalkyl radical, a ($C_1$ to $C_4$)-hydroxyalkoxy radical, a ($C_1$ to $C_4$)-acetylaminoalkoxy radical, a mesylamino-($C_1$ to $C_4$)-alkoxy radical or a ($C_1$ to $C_4$)-carbamoyl-aminoalkoxy radical; and $G^4$ is a hydrogen atom, a halogen atom or a ($C_1$ to $C_4$)-alkyl radical, or when $G^3$ and $G^4$ are in ortho position to one another, they may jointly form a bridging α,ω-alkylenedioxo group such as an ethylenedioxy group.

Especially preferred p-phenylenediamines of the formula (E1) are chosen from one or more compounds of the group formed by p-phenylenediamine, p-toluoylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethypaniline, N,N-bis-(β-hydroxyethyl)-p-phenylenediamine, 4-N,N-bis-(β-hydroxyethyl)amino-2-methylaniline, 4-N,N-bis-(β-hydroxyethyl)amino-2-chloroaniline, 2-(β-hydroxyethyl)-p-phenylenediamine, 2-(α,β-dihydroxyethyl)-p-phenylenediamine, 2-fluoro-p-phenylenediamine, 2-isopropyl-p-phenylenediamine, N-(β-hydroxypropyl)-p-phenylenediamine, 2-hydroxymethyl-p-phenylene-diamine, N,N-dimethyl-3-methyl-p-phenylenediamine, N,N-(ethyl-β-hydroxyethyl)-p-phenylenediamine, N-(β,γ-dihydroxypropyl)-p-phenylenediamine, N-(4'-aminophenyl)-p-phenylenediamine, N-phenyl-p-phenylenediamine, 2-(β-hydroxyethyloxy)-p-phenylenediamine, 2-(β-acetylaminoethyloxy)-p-phenylenediamine, N-(β-methoxyethyl)-p-phenylenediamine, N-(4-amino-3-methylphenyl)-N-[3-(1H-imidazol-1-yl)propyl]amine, 5,8-diaminobenzo-1,4-dioxane as well as their physiologically tolerable salts.

Most especially preferred p-phenylenediamine derivatives of formula (E1) according to the invention are chosen from at least one compound of the group p-phenylenediamine, p-toluoylenediamine, 2-(β-hydroxyethyl)-p-phenylenediamine, 2-(α,β-dihydroxyethyl)-p-phenylenediamine, N,N-bis-(β-hydroxyethyl)-p-phenylenediamine, N-(4-amino-3-methylphenyl)-N-[3-(1H-imidazol-1-yl)propyl]amine, as well as the physiologically tolerable salts of these compounds.

It may also be preferable according to the invention to use compounds having at least two aromatic nuclei substituted with amino and/or hydroxy groups as the developer component for dyeing the substrate.

Of the binuclear developer components, in particular, compounds corresponding to the following formula (E2) and their physiologically tolerable salts are suitable—

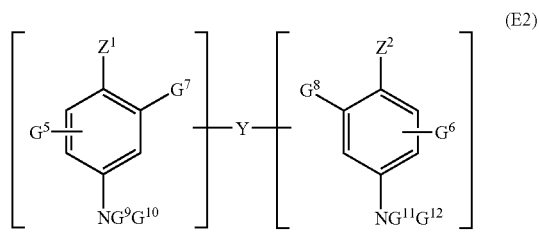

wherein $Z^1$ and $Z^2$ are independently a hydroxy radical or an $NH_2$ radical, optionally substituted by a ($C_1$ to $C_4$)-alkyl radical, by a ($C_1$ to $C_4$)-hydroxyalkyl radical and/or by a bridge Y, or optionally being part of a bridging ring system, the bridge Y is an alkylene group with 1 to 14 carbon atoms such as a linear or branched alkylene chain or an alkylene ring, which may be interrupted or terminated by one or more nitrogenous groups and/or one or more heteroatoms, such as oxygen, sulfur or nitrogen atoms and may optionally be substituted by one or more hydroxy radicals or ($C_1$ to $C_8$) alkoxy radicals or a direct bond; $G^5$ and $G^6$ are independently a hydrogen or halogen atom, a ($C_1$ to $C_4$)-alkyl radical, a ($C_1$ to $C_4$)-monohydroxyalkyl radical, a ($C_2$ to $C_4$)-polyhydroxyalkyl radical, a ($C_1$ to $C_4$)-aminoalkyl radical or a direct bond to the Y bridge; $G^7$, $G^8$, $G^9$, $G^{10}$, $G^{11}$ and $G^{12}$ are independently a hydrogen atom, a direct bond to the Y bridge or a ($C_1$ to $C_4$)-alkyl radical; with the provision that the compounds of formula (E2) contain only one Y bridge per molecule.

Substituents used in formula (E2) are defined according to the invention as in the above implementations.

Preferred binuclear developer components of formula (E2) are chosen from N,N'-bis-(β-hydroxyethyl)-N,N'-bis-(4'-aminophenyl)-1,3-diaminopropan-2-ol, hydroxyethyl)-N, N'-bis-(4'aminophenyl)ethylenediamine, N,N'-bis-(4'-amino-phenyl)tetramethylenediamine, N,N'-bis-(4-(methylamino)phenyl)tetramethylenediamine, N,N'-diethyl-N,N'-bis(4'-amino-3'-methylphenyl)ethylenediamine, bis-(2-hydroxy-5-aminophenyl)methane, N,N'-bis-(4'-aminophenyl)-1,4-diazacycloheptane, N,N'-bis-(2-hydroxy-5-aminobenzyl)piperazine, N-(4'-aminophenyl)-p-phenylenediamine and 1,10-bis-(2',5'-diaminophenyl)-1,4,7,10-tetraoxadecane as well as their physiologically tolerable salts.

Most especially preferred binuclear developer components of formula (E2) are chosen from N,N'-bis-(β-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane or one of the physiologically tolerable salts of these compounds.

In addition, it may be preferable according to the invention to use as the developer component a p-aminophenol derivative or one of its physiologically tolerable salts for dyeing the keratin-containing fibers to be decolored. Especially preferred are p-aminophenol derivatives of formula (E3)—

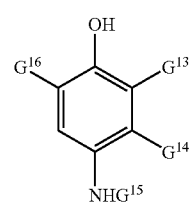

wherein $G^{13}$ is a hydrogen atom, a halogen atom, a ($C_1$ to $C_4$)-alkyl radical, a ($C_1$ to $C_4$)-monohydroxyalkyl radical, a ($C_2$ to $C_4$)-polyhydroxyalkyl radical, a ($C_1$ to $C_4$)-alkoxy-($C_1$ to $C_4$)-alkyl radical, a ($C_1$ to $C_4$)-aminoalkyl radical, a hydroxy-($C_1$ to $C_4$)-alkylamino radical, a ($C_1$ to $C_4$)-hydroxyalkoxy radical, a ($C_1$ to $C_4$)-hydroxyalkyl-($C_1$ to $C_4$)-aminoalkyl radical or a di-($C_1$ to $C_4$)-alkylamino-($C_1$ to $C_4$)-alkyl radical; $G^{14}$ is a hydrogen or halogen atom, a ($C_1$ to $C_4$)-alkyl radical, a ($C_1$ to $C_4$)-monohydroxyalkyl radical, a ($C_2$ to $C_4$)- polyhydroxyalkyl radical, a ($C_1$ to $C_4$)-alkoxy-($C_1$ to $C_4$)-alkyl radical, a ($C_1$ to $C_4$)-aminoalkyl radical or a ($C_1$ to $C_4$)-cyanoalkyl radical; $G^{15}$ is hydrogen, a ($C_1$ to $C_4$)-alkyl radical, a ($C_1$ to $C_4$)-monohydroxyalkyl radical, a ($C_2$ to $C_4$)-polyhydroxyalkyl radical, a phenyl radical or a benzyl radical; and $G^{16}$ is hydrogen or a halogen atom.

Substituents used in formula (E3) are defined according to the invention as in the above implementations.

Preferred p-aminophenols of formula (E3) include in particular p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(β-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-(α,β-dihydroxyethyl)phenol, 4-amino-2-fluorophenol, 4-amino-2-chlorophenol, 4-amino-2,6-dichlorophenol, 4-amino-2-(diethylaminomethyl)phenol as well as their physiologically tolerable salts.

Most especially preferred compounds of formula (E3) include p-aminophenol, 4-amino-3-methylphenol, 4-amino-2-aminomethylphenol, 4-amino-2-(α,β-dihydroxyethyl)phenol and 4-amino-2-(diethylaminomethyl)phenol.

Furthermore, the developer component may be chosen from o-aminophenol and its derivatives, for example, 2-amino-4-methylphenol, 2-amino-5-methylphenol or 2-amino-4-chlorophenol.

In addition, the developer component for dyeing keratin-containing fibers to be decolored may be chosen from heterocyclic developer components such as pyrimidine derivatives, pyrazole derivatives, pyrazolopyrimidine derivatives and/or their physiologically tolerable salts.

Preferred pyrimidine derivatives according to the invention are chosen from compounds according to formula (E4) and/or their physiologically tolerable salts

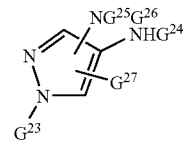

(E4)

wherein $G^{17}$, $G^{18}$ and $G^{19}$ are independently hydrogen, a hydroxy group, a ($C_1$ to $C_4$)-alkoxy group or an amino group; and $G^{20}$ is a hydroxy group or an —$NG^{21}G^{22}$ group, in which $G^{21}$ and $G^{22}$, are independently hydrogen, a ($C_1$ to $C_4$)-alkyl group, or a ($C_1$ to $C_4$)-monohydroxyalkyl group, with the provision that two of the $G^{17}$, $G^{18}$, $G^{19}$ and $G^{20}$ groups denote a hydroxy group, and at most two of the $G^{17}$, $G^{18}$ and $G^{19}$ groups stand for a hydrogen atom. It is again preferable if, according to formula (E4), at least two of the $G^{17}$, $G^{18}$, $G^{19}$ and $G^{20}$ groups stand for an —$NG^{21}G^{22}$ group, and at most two of the $G^{17}$, $G^{18}$, $G^{19}$ and $G^{20}$ groups stand for a hydroxy group.

Especially preferred pyrimidine derivatives include 2,4,5,6-tetraminopyrimidine, 4-hydroxy-2,5,6-triamiopyrimidine, 2-hydroxy-4,5,6-triaminopyrimidine, 2-dimethylamino-4,5,6-triaminopyrimidine, 2,4-dihydroxy-5,6-diaminopyriidine and 2,5,6-triaminopyrimidine.

Preferred pyrazole derivatives are selected according to the invention from compounds according to formula (E5)

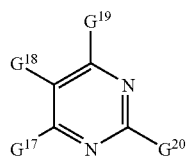

(E5)

wherein $G^{23}$, $G^{24}$, $G^{25}$ are independently hydrogen, a ($C_1$ to $C_4$)-alkyl group, a ($C_1$ to $C_4$)-monohydroxyalkyl group, a ($C_2$ to $C_4$)-polyhydroxyalkyl group, an optionally substituted aryl group or an optionally substituted aryl-($C_1$ to $C_4$)-alkyl group, with the provision that when $G^{25}$ stands for a hydrogen atom, $G^{26}$ in addition to the aforementioned groups may also stand for an —$NH_2$ group; $G^{26}$ is hydrogen, a ($C_1$ to $C_4$)-alkyl group, a ($C_1$ to $C_4$)-monohydroxyalkyl group or a ($C_2$ to $C_4$)-polyhydroxyalkyl group; and $G^{27}$ is hydrogen, an optionally substituted aryl group, a ($C_1$ to $C_4$)-alkyl group or a ($C_1$ to $C_4$)-monohydroxyalkyl group, in particular hydrogen or a methyl group.

In formula (E5) the —$NG^{25}G^{26}$ radical preferably binds at position 5, and the $G^{27}$ radical binds at position 3 of the pyrazole ring.

Especially preferred pyrazole derivatives include 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1 methylpyrazole, 4,5-diamino-3-hydroxymethyl-1-isopropylpyrazole, 4,5-diamino-3-methyl-1-isopropylpyrazole, 4-amino-5-(β-aminoethyl)amino-1,3-dimethylpyrazole as well as their physiologically tolerable salts.

Preferred pyrazolopyrimidine derivatives include in particular the derivatives of pyrazolo[1,5-a]pyrimidine of the following formula (E6) and its tautomeric forms, if there is a tautomeric equilibrium:

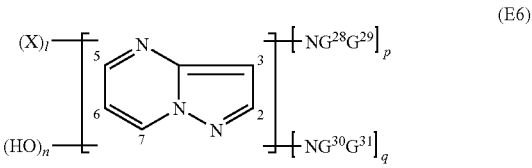

(E6)

wherein $G^{28}$, $G^{29}$ and $G^{30}$, $G^{31}$ are independently hydrogen, a ($C_1$ to $C_4$)-alkyl radical, an aryl radical, a ($C_1$ to $C_4$)-monohydroxyalkyl radical, a ($C_2$ to $C_4$)-polyhydroxyalkyl radical, a ($C_1$ to $C_4$)-alkoxy-($C_1$ to $C_4$)-alkyl radical, a ($C_1$ to $C_4$)-aminoalkyl radical, optionally protected by an acetyl ureido radical or a sulfonyl radical, a ($C_1$ to $C_4$)-alkylamino ($C_1$ to $C_4$)-alkyl radical, a di($C_1$ to $C_4$)-alkyl ($C_1$ to $C_4$)-aminoalkyl radical, where the dialkyl radicals optionally form a carbon cycle or a heterocycle with 5 or 6 chain members, a ($C_1$ to $C_4$)-monohydroxyalkyl radical or a di($C_1$ to $C_4$)-hydroxylalkyl-($C_1$ to $C_4$)-aminoalkyl radical; the X radicals are independently hydrogen, a ($C_1$ to $C_4$)-alkyl radical, an aryl radical, a ($C_1$ to $C_4$)-monohydroxyalkyl radical, a ($C_2$ to $C_4$)-polyhydroxyalkyl radical, a ($C_1$ to $C_4$)-aminoalkyl radical, a ($C_1$ to $C_4$)-alkylamino-($C_1$ to $C_4$)-alkyl radical, a di($C_1$ to $C_4$)-alkyl-($C_1$ to $C_4$)-aminoalkyl radical, where the dialkyl radicals may optionally form a carbon cycle or a heterocycle with five or six chain members, a ($C_1$ to $C_4$)-hydroxyalkyl or di($C_1$ to $C_4$)-hydroxyalkylamino-($C_1$ to $C_4$)-alkyl radical, an amino radical, a ($C_1$ to $C_4$)-alkyl or di($C_1$ to $C_4$)-hydroxyalkylamino radical, a halogen atom, a carboxylic acid group or a sulfonic acid group; i is 0, 1, 2 or 3; p is 0 or 1; q is 0 or 1; and n is 0 or 1; with the provision that the sum of p+q is not equal to 0 when p+q is equal to 2, n has a value of 0, and the $NG^{28}G^{29}$ and $NG^{30}G^{31}$ groups occupy the positions (2, 3); (5, 6); (6, 7); (3, 5) or (3, 7);

when p+q is equal to 1, n has a value of 1, and the $NG^{28}G^{29}$ group (or the $NG^{30}G^{31}$ group) and the OH group occupy the positions (2, 3); (5, 6); (6, 7); (3, 5) or (3, 7).

Substituents used in formula (E7) according to the invention are defined as in the above implementations.

If the pyrazolo[1,5-a]pyrimidine of formula (E6) given above has a hydroxy group in one of the positions 2, 5 or 7 of the ring system, there is a tautomeric equilibrium, which is represented in the following scheme, for example:

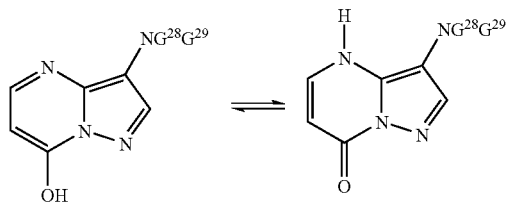

Pyrazolo[1,5-a]pyrimidines of formula (E7) given above include pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)-(2-hydroxyethyl)amino]ethanol; 2-[(7-aminopyrazolo[1,5-a]pyrimidin-3-yl)-(2-hydroxyethyl)amino]ethanol; 5,6-dimethylpyrazolo[1,5-a]pyrimidine-3,7-diamine; 2,6-dimethylpyrazolo[1,5-a]pyrimidin-3,7-diamine; 3-amino-7-dimethylamino-2,5-dimethylpyrazolo[1,5-a]pyrimidine; as well as their physiologically tolerable salts and their tautomeric forms, if there is a tautomeric equilibrium.

Pyrazolo[1,5-a]pyrimidines of formula (E6) given above can be synthesized as described in the literature by cyclization, starting from an aminopyrazole or from hydrazine.

Most especially preferred developer components for dyeing keratin-containing fibers to be decolored include at least one compound of the group formed by p-phenylenediamine, p-toluoylenediamine, 2-(β-hydroxyethyl)-p-phenylenediamine, 2-(α,β-dihydroxyethyl)-p-phenylenediamine, N,N-bis-(β-hydroxyethyl)-p-phenylenediamine, N-(4-amino-3-methylphenyl)-N-[3-(1H-imidazol-1-yl)propyl]amine, N,N'-bis-(β-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecene, p-aminophenol, 4-amino-3-methylphenol, 4-amino-2-aminomethylphenol, 4-amino-2-(α,β-dihydroxyethyl)phenol and 4-amino-2-(dimethylaminomethyl)phenol, 4,5-diamino-1-(β-hydroxyethyl)pyrazole, 2,4,5,6-tetraminopyrimidine, 4-hydroxy-2,5,6-triaminopyrimidine, 2-hydroxy-4,5,6-triaminopyrimidine as well as the physiologically tolerable salts of these compounds.

Examples of radicals mentioned as substituents of the compounds of formulas (E1) to (E6) are listed as follows: examples of ($C_1$ to $C_4$)-alkyl radicals include the groups —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$. Inventive examples of ($C_1$ to $C_4$)-alkoxy radicals include —$OCH_3$, —$OCH_2CH_3$, —$OCH_2CH_2CH_3$, —$OCH(CH_3)_2$, —$OCH_2CH_2CH_2CH_3$, —$OCH_2CH(CH_3)_2$, —$OCH(CH_3)CH_2CH_3$, —$OC(CH_3)_3$, in particular a methoxy group or an ethoxy group.

In addition, preferred examples of ($C_1$ to $C_4$)-monohydroxyalkyl group include —$CH_2OH$, —$CH_2CH_2OH$, —$CH_2CH_2CH_2OH$, —$CHCH(OH)CH_3$, —$CH_2CH_2CH_2CH_2OH$, where the group —$CH_2CH_2OH$ is preferred.

An especially preferred example of a ($C_2$ to $C_4$)-polyhydroxyalkyl group is 1,2-dihydroxyethyl.

Examples of halogen atoms include F, Cl or Br atoms, with Cl atoms most especially preferred.

Examples of nitrogenous groups include in particular $NH_2$ ($C_1$ to $C_4$)-monoalkylamino groups, ($C_1$ to $C_4$)-dialkylamino groups, ($C_1$ to $C_4$)-trialkylammonium groups, ($C_1$ to $C_4$)-monohydroxyalkylamino groups, imidazolinium and $NH_3^+$.

Examples of ($C_1$ to $C_4$)-monoalkylamino groups include —$NHCH_3$, —$NHCH_2CH_3$, —$NHCH_2CH_2CH_3$, —$NHCH(CH_3)_2$.

Examples of ($C_1$ to $C_4$)-dialkylamino groups include —$N(CH_3)_2$, —$N(CH_2CH_3)_2$.

Examples of ($C_1$ to $C_4$)-trialkylammonium groups include —$N^+(CH_3)_3$, —$N^+(CH_3)_2(CH_2CH_3)$, —$N^+(CH_3)(CH_2CH_3)_2$.

Examples of ($C_1$ to $C_4$)-hydroxyalkylamino radicals include —NH—$CH_2CH_2OH$, —NH—$CH_2CH_2OH$, —NH—$CH_2CH_2CH_2OH$, —NH—$CH_2CH_2CH_2OH$.

Examples of ($C_1$ to $C_4$)-alkoxy-($C_1$ to $C_4$)-alkyl groups include the groups —$CH_2CH_2$—O—$CH_3$, —$CH_2CH_2CH_2$—O—$CH_3$, —$CH_2CH_2$—O—$CH_2CH_3$, —$CH_2CH_2CH_2$—O—$CH_2CH_3$, —$CH_2CH_2$—O—$CH(CH_3)$, —$CH_2CH_2CH_2$—O—$CH(CH_3)$.

Examples of hydroxy ($C_1$ to $C_4$)-alkoxy radicals include —O—$CH_2OH$, —O—$CH_2CH_2OH$, —O—$CH_2CH_2CH_2OH$, —O—$CHCH(OH)CH_3$, —O—$CH_2CH_2CH_2CH_2OH$.

Examples of ($C_1$ to $C_4$)-acetylaminoalkoxy radicals include —O—$CH_2NHC(O)CH_3$, —O—$CH_2CH_2NHC(O)CH_3$, —O—$CH_2CH_2CH_2NHC(O)CH_3$, —O—$CH_2CH(NHC(O)CH_3)CH_3$, —O—$CH_2CH_2CH_2CH_2NHC(O)CH_3$.

Examples of ($C_1$ to $C_4$)-carbamoylaminoalkoxy radicals include —O—$CH_2CH_2$—NH—C(O)—$NH_2$, —O—$CH_2CH_2CH_2$—NH—C(O)—$NH_2$, —O—$CH_2CH_2CH_2CH_2$—NH—C(O)—$NH_2$.

Examples of ($C_1$ to $C_4$)-aminoalkyl radicals include —$CH_2NH_2$, —$CH_2CH_2NH_2$, —$CH_2CH_2CH_2NH_2$, —$CH_2CH(NH_2)CH_3$, —$CH_2CH_2CH_2CH_2NH_2$.

Examples of ($C_1$ to $C_4$)-cyanoalkyl radicals include —$CH_2CN$, —$CH_2CH_2CN$, —$CH_2CH_2CH_2CN$.

Examples of ($C_1$ to $C_4$)-hydroxyalkylamino ($C_1$ to $C_4$)-alkyl radicals include —$CH_2CH_2NH$—$CH_2CH_2OH$, —$CH_2CH_2CH_2NH$—$CH_2CH_2OH$, —$CH_2CH_2NH$—$CH_2CH_2CH_2OH$, —$CH_2CH_2CH_2NH$—$CH_2CH_2CH_2OH$.

Examples of di($C_1$ to $C_4$)-hydroxyalkylamino ($C_1$ to $C_4$)-alkyl radicals include —$CH_2CH_2N(CH_2CH_2OH)_2$, —$CH_2CH_2CH_2N(CH_2CH_2OH)_2$, —$CH_2CH_2N(CH_2CH_2CH_2OH)_2$, —$CH_2CH_2CH_2N(CH_2CH_2CH_2OH)_2$.

The phenyl group is one example of an aryl group.

Examples of aryl-($C_1$ to $C_4$)-alkyl groups include the benzyl group and the 2-phenylethyl group.

Coupler components alone do not develop any significant coloration within the scope of oxidative dyeing but instead always require the presence of developer components. It is therefore preferable according to the invention to additionally use at least one coupler component for dyeing the keratin-containing fibers to be decolored when using at least one developer component.

Coupler components in the sense of the invention allow at least one substitution of a chemical radical of the coupler by the oxidized form of the developer component. In doing so, a covalent bond is formed between the coupler component and the developer component. Couplers are preferably cyclic compounds having at least two groups on the ring, selected from (i) optionally substituted amino groups and/or (ii) hydroxy groups. If the cyclic compound is a six-membered ring (preferably aromatic), then said groups are preferably in ortho position or meta position to one another.

Inventive coupler components for dyeing keratin-containing fibers to be decolored preferably include:
- m-aminophenol and/or its derivatives,
- m-diaminobenzene and/or its derivatives,
- o-diaminobenzene and/or its derivatives,
- o-aminophenol derivatives such as o-aminophenol,
- naphthalene derivatives having at least one hydroxy group,
- di- and/or trihydroxybenzene and/or their derivatives,
- pyridine derivatives,
- pyrimidine derivatives,
- monohydroxyindole derivatives and/or monoaminoindole derivatives,
- monohydroxyindoline derivatives and/or monoaminoindoline derivatives,
- pyrazolone derivatives, such as 1-phenyl-3-methylpyrazol-5-one,
- morpholine derivatives, such as 6-hydroxybenzomorpholine or 6-aminobenzomorpholine,
- quinoxaline derivatives, such as 6-methyl-1,2,3,4-tetrahydroquinoxaline, mixtures of two or more compounds of one or more of these classes are also inventive within this scope of this embodiment.

The m-aminophenols and/or their derivatives to be used according to the invention are preferably chosen from at least one compound of the formula (K1) and/or at least one physiologically tolerable salt of a compound according to formula (K1)

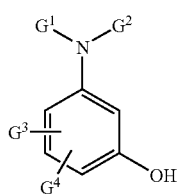

(K1)

wherein $G^1$ and $G^2$ are independently hydrogen, a ($C_1$ to $C_4$)-alkyl group, a ($C_3$ to $C_6$)-cycloalkyl group, a ($C_2$ to $C_4$)-alkenyl group, a ($C_1$ to $C_4$)-monohydroxyalkyl group, a ($C_2$ to $C_4$)-polyhydroxyalkyl group, a ($C_2$ to $C_4$)-perfluoroacyl group, an aryl-($C_1$ to $C_6$)-alkyl group, an amino-($C_1$ to $C_6$)-alkyl group, a ($C_1$ to $C_6$)-dialkylamino-($C_1$ to $C_6$)-alkyl group or a ($C_1$ to $C_6$)-alkoxy-($C_1$ to $C_6$)-alkyl group, in which $G^1$ and $G^2$ together with the nitrogen atom may form a five-membered, six-membered or seven-membered ring; and $G^3$ and $G^4$ are independently hydrogen, a halogen atom, a ($C_1$ to $C_4$)-alkyl group, a ($C_1$ to $C_4$)-alkoxy group, a hydroxy group, a ($C_1$ to $C_4$)-monohydroxyalkyl group, a ($C_2$ to $C_4$)-polyhydroxyalkyl group, a hydroxy-($C_1$ to $C_4$)-alkoxy group, a ($C_1$ to $C_6$)-alkoxy-($C_2$ to $C_6$)-alkoxy group, an aryl group or a heteroaryl group.

Especially preferred m-aminophenol coupler components include at least one compound of the group formed by m-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-(diethylamino)phenol, N-cyclopentyl-3-aminophenol, 1,3-dihydroxy-5-(methylamino)benzene, 3-ethylamino-4-methylphenol, 2,4-dichloro-3-aminophenol and the physiologically tolerable salts of all the compounds listed above.

The m-diaminobenzenes and/or their derivatives that may be used according to the invention are preferably chosen from at least one compound of the formula (K2) and/or at least one physiologically tolerable salt of a compound according to formula (K2)

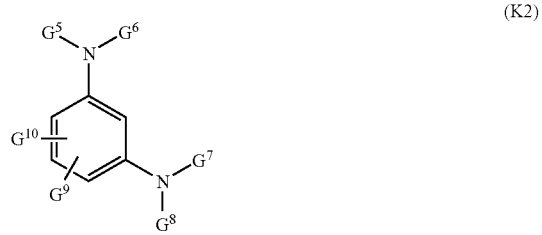

(K2)

wherein $G^5$, $G^6$, $G^7$ and $G^8$ are independently hydrogen, a ($C_1$ to $C_4$)-alkyl group, a ($C_3$ to $C_6$)-cycloalkyl group, a ($C_2$ to $C_4$)-alkenyl group, a ($C_1$ to $C_4$)-monohydroxyalkyl group, a ($C_2$ to $C_4$)-polyhydroxyalkyl group, a ($C_1$ to $C_4$)-alkoxy ($C_1$ to $C_4$)-alkyl group, an aryl-($C_1$ to $C_4$)-alkyl group, a heteroaryl-($C_1$ to $C_4$)-alkyl group, a ($C_2$ to $C_4$)-perfluoroacyl group, or together with a nitrogen atom, form a five-membered or six-membered heterocycle; and $G^9$ and $G^{10}$ are independently hydrogen, a halogen atom, a ($C_1$ to $C_4$)-alkyl group, an ω-(2,4-diaminophenyl)-($C_1$ to $C_4$)-alkyl group, an ω-(2,4-diaminophenyloxy)-($C_1$ to $C_4$)-alkoxy group, a ($C_1$ to $C_4$)-alkoxy group, a hydroxy group, a ($C_1$ to $C_4$)-alkoxy ($C_2$ to $C_4$)-alkoxy group, an aryl group, a heteroaryl group, a ($C_1$ to $C_4$)-monohydroxyalkyl group, a ($C_2$ to $C_4$)-polyhydroxyalkyl group, a hydroxy-($C_1$ to $C_4$)-alkoxy group.

Especially preferred m-diaminobenzene coupler components include at least one compound of the group formed by m-phenylenediamine, 2-(2,4-diaminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)

ethanol, 2-[3-morpholin-4-ylphenyl)amino]ethanol, 3-amino-4-(2-methoxyethoxy)-5-methylphenylamine, 1-amino-3-bis-(2'-hydroxyethyl)aminobenzene and the physiologically tolerable salts of all the compounds listed above.

The o-diaminobenzenes and/or their derivative that may be used according to the invention are preferably selected from at least one compound of formula (K3) and/or from at least one physiologically tolerable salt of a compound according to formula (K3)

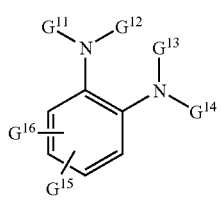

(K3)

wherein $G^{11}$, $G^{12}$, $G^{13}$ and $G^{14}$ are independently hydrogen, a ($C_1$ to $C_4$)-alkyl group, a ($C_3$ to $C_6$)-cycloalkyl group, a ($C_2$ to $C_4$)-alkenyl group, a ($C_1$ to $C_4$)-monohydroxyalkyl group, a ($C_2$ to $C_4$)-polyhydroxyalkyl group, a ($C_1$ to $C_4$)-alkoxy-($C_1$ to $C_4$) alkyl group, an aryl-($C_1$ to $C_4$)-alkyl group, a heteroaryl-($C_1$ to $C_4$)-alkyl group, a ($C_2$ to $C_4$)-perfluoroacyl group or, together with the nitrogen atom, form a five-membered or six-membered heterocycle; and $G^{15}$ and $G^{16}$ are independently hydrogen, a halogen atom, a carboxy group, a ($C_1$ to $C_4$)-alkyl group, a ($C_1$ to $C_4$)-alkoxy group, a hydroxy group, a ($C_1$ to $C_4$)-monohydroxyalkyl group, a ($C_2$ to $C_4$)-polyhydroxyalkyl group, a hydroxy-($C_1$ to $C_4$)-alkoxy group.

Especially preferred o-diaminobenzene coupler components include at least one compound of the group formed by 3,4-diaminobenzoic acid and 2,3-diamino-1-methylbenzene and the physiologically tolerable salts of all the compounds listed above.

Preferred di- and/or trihydroxybenzenes and their derivatives include at least one compound of the group formed by resorcinol, resorcinol monomethyl ether, 2-methylresorcinol, 5-methylresorcinol, 2,5-dimethylresorcinol, 2-chlororesorcinol, 4-chlororesorcinol, pyrogallol and 1,2,4-trihydroxybenzene.

Pyridine derivatives that may be used according to the invention preferably include at least one compound of formula (K4) and/or at least one physiologically tolerable salt of a compound according to formula (K4)

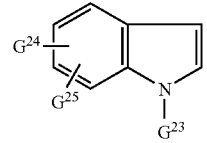

(K4)

wherein $G^{17}$ and $G^{18}$ are independently a hydroxy group or an —$NG^{21}G^{22}$ group, in which $G^{21}$ and $G^{22}$ are independently hydrogen, a ($C_1$ to $C_4$)-alkyl group, a ($C_3$ to $C_6$)-cycloalkyl group, a ($C_2$ to $C_4$)-alkenyl group, an aryl group, a ($C_1$ to $C_4$)-monohydroxyalkyl group, a ($C_2$ to $C_4$)-polyhydroxyalkyl group, a ($C_1$ to $C_4$) alkoxy-(C to $C_4$)-alkyl group, an aryl-($C_1$ to $C_4$)-alkyl group, a heteroaryl-($C_1$ to $C_4$)-alkyl group; and $G^{19}$ and $G^{20}$ are independently hydrogen, a halogen atom, a ($C_1$ to $C_4$)-alkyl group or a ($C_1$ to $C_4$)-alkoxy group.

It is preferable if, according to formula (K4), the $G^{17}$ and $G^{18}$ radicals are in ortho position or in meta position to one another.

Especially preferred pyridine derivatives include at least one compound of the group formed by 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 3,4-diaminopyridine, 2-(2-methoxyethyl)amino-3-amino-6-methoxypyridine, 2-(4'-methoxyphenyl)amino-3-aminopyridine and the physiologically tolerable salts of the aforementioned compounds.

Preferred naphthalene derivatives having at least one hydroxy group induce at least one compound of the group formed by 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene.

Indole derivatives that may be used according to the invention preferably include at least one compound of formula (K5) and/or at least one physiologically tolerable salt of a compound according to formula (K5):

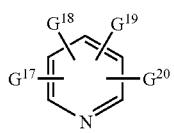

(K5)

wherein $G^{23}$ is hydrogen, a ($C_1$ to $C_4$)-alkyl group, a ($C_3$ to $C_6$)-cycloalkyl group, a ($C_2$ to $C_4$)-alkenyl group, a ($C_1$ to $C_4$)-monohydroxyalkyl group, a ($C_2$ to $C_4$)-polyhydroxyalkyl group, or an aryl-($C_1$ to $C_4$)-alkyl group; $G^{24}$ is a hydroxy group or an —$NG^{26}G^{27}$ group, in which $G^{26}$ and $G^{27}$ independently are hydrogen, a ($C_1$ to $C_4$)-alkyl group, a ($C_3$ to $C_6$)-cycloalkyl group, a ($C_2$ to $C_4$)-alkenyl group, a ($C_1$ to $C_4$)-monohydroxyalkyl group, or a ($C_2$ to $C_4$)-polyhydroxyalkyl group; and $G^{25}$ is hydrogen, a halogen atom or a ($C_1$ to $C_4$)-alkyl group, with the provision that $G^{24}$ in meta position or ortho position binds to the structural fragment $NG^{23}$ of the formula.

Especially preferred indole derivatives include at least one compound of the group formed by 4-hydroxyindole, 6-hydroxyindole and 7-hydroxyindole and the physiologically tolerable salts of the compounds listed above.

Indole derivatives that may be used according to the invention preferably include at least one compound of the formula (K6) and/or at least one physiologically tolerable salt of a compound according to formula (K6)

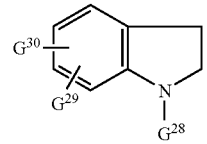

(K6)

wherein $G^{28}$ is hydrogen, a ($C_1$ to $C_4$)-alkyl group, a ($C_3$ to $C_6$)-cycloalkyl group, a ($C_2$ to $C_4$)-alkenyl group, a ($C_1$ to $C_4$)-monohydroxyalkyl group, a ($C_2$ to $C_4$)-polyhydroxyalkyl group, an aryl-($C_1$ to $C_4$)-alkyl group; $G^{29}$ is a hydroxy group or an —$NG^{31}G^{32}$ group, in which $G^{31}$ and $G^{32}$, independently of one another, stand for a hydrogen atom, a ($C_1$ to $C_4$)-alkyl group, a ($C_3$ to $C_6$)-cycloalkyl group, a ($C_2$ to $C_4$)-alkenyl group, a ($C_1$ to $C_4$)-monohydroxyalkyl group, a ($C_2$ to $C_4$)-polyhydroxyalkyl group; and $G^{30}$ is hydrogen, a halogen atom or a ($C_1$ to $C_4$)-alkyl group, with the provision that $G^{29}$ binds to the structural fragment $NG^{28}$ of the formula in meta position or ortho position.

Especially preferred indoline derivatives include at least one compound of the group formed by 4-hydroxyindoline, 6-hydroxyindoline and 7-hydroxyindoline and the physiologically tolerable salts of the aforementioned compounds.

Preferred pyrimidine derivatives include at least one compound of the group formed by 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine and the physiologically tolerable salts of the compounds listed above.

For dyeing keratin-containing fibers to be decolored, especially preferred coupler components according to the invention include m-aminophenol, 5-amino-2-methylphenol, 3-amino-2-chloro-6-methylphenol, 2-hydroxy-4-aminophenoxyethanol, 5-amino-4-chloro-2-methylphenol, 5-(2'-hydroxyethyl)amino-2-methylphenol, 2,4-dichloro-3-aminophenol, o-aminophenol, m-phenylenediamine, 2-(2,4-diaminophenoxy)ethanol, 1,3-bis(2,4-diaminophenoxy) propane, 1-methoxy-2-amino-4-(2'-hydroxyethylamino) benzene, 1,3-bis(2,4-diaminophenyl)propane, 2,6-bis(2'-hydroxyethylamino)-1-methylbenzene, 2-({3-[(2-hydroxyethypamino]-4-methoxy-5-methylphenyl}amino) ethanol, 2-({3-[(2-hydroxyethypamino]-2-methoxy-5-methylphenyl}amino)ethanol, 2-({3-[(2-hydroxyethyl) amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2'-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or the physiologically tolerable salts of the compounds listed above.

The coupler components are preferably used in an amount of 0.005 to 20 wt %, preferably 0.1 to 5 wt %, each based on the oxidative dyes used for dyeing keratin-containing fibers to be decolored.

Developer components and coupler components are generally used in approximately molar amounts relative to one another. If molar use has also proven expedient, then a certain excess of individual oxidative dye precursors is not a disadvantage, so that developer components and coupler components may be in a molar ratio of 1:0.5 to 1:3, in particular 1:1 to 1:2.

Examples of radicals mentioned as substituents of the compounds of formulas (K1) to (K6) are listed below: examples of ($C_1$ to $C_4$)-alkyl radicals include —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$.

Inventive examples of ($C_3$ to $C_6$)-cycloalkyl groups include the cyclopropyl group, the cyclopentyl group and the cyclohexyl group.

Inventive examples of ($C_1$ to $C_4$)-alkoxy radicals include —$OCH_3$, —$OCH_2CH_3$, —$OCH_2CH_2CH_3$, —$OCH(CH_3)_2$, —$OCH_2CH_2CH_2CH_3$, —$OCH_2CH(CH_3)_2$, —$OCH(CH_3)CH_2CH_3$, —$OC(CH_3)_3$, in particular a methoxy group or an ethoxy group.

In addition, preferred examples of a ($C_1$ to $C_4$)-monohydroxyalkyl group include —$CH_2OH$, —$CH_2CH_2OH$, —$CH_2CH_2CH_2OH$, —$CHCH(OH)CH_3$, —$CH_2CH_2CH_2CH_2OH$, with —$CH_2CH_2OH$ preferred.

An especially preferred example of a ($C_2$ to $C_4$)-polyhydroxyalkyl group is 1,2-dihydroxyethyl.

Examples of halogen atoms include F, Cl or Br atoms, with Cl atoms being most especially preferred.

Examples of nitrogenous groups include in particular —$NH_2$ ($C_1$ to $C_4$)-monoalkylamino groups, ($C_1$ to $C_4$)-dialkylamino groups, ($C_1$ to $C_4$)-trialkylammonium groups, ($C_1$ to $C_4$)-monohydroxyalkylamino groups, imidazolinium and —$NH_3^+$.

Examples of ($C_1$ to $C_4$)-monoalkylamino groups include —$NHCH_3$, —$NHCH_2CH_3$, —$NHCH_2CH_2CH_3$, —$NHCH(CH_3)_2$.

Examples of the ($C_1$ to $C_4$)-dialkylamino group include —$N(CH_3)_2$, —$N(CH_2CH_3)_2$.

Examples of ($C_1$ to $C_4$)-alkoxy-($C_1$ to $C_4$)-alkyl groups include —$CH_2CH_2$—O—$CH_3$, —$CH_2CH_2CH_2$—O—$CH_3$, —$CH_2CH_2$—O—$CH_2CH_3$, —$CH_2CH_2CH_2$—O—$CH_2CH_3$, —$CH_2CH_2$—O—$CH(CH_3)_2$, —$CH_2CH_2CH_2$—O—$CH(CH_3)_2$.

Examples of ($C_1$ to $C_4$)-alkoxy-($C_1$ to $C_4$)-alkoxy groups include —O—$CH_2CH_2$-β-$CH_3$, —O—$CH_2CH_2CH_2$—O—$CH_3$, —O—$CH_2CH_2$—O—$CH_2CH_3$, —O—$CH_2CH_2CH_2$—O—$CH_2CH_3$, —O—$CH_2CH_2$—O—$CH(CH_3)_2$, —O—$CH_2CH_2CH_2$—O—$CH(CH_3)_2$.

Examples of hydroxy-($C_1$ to $C_4$)-alkoxy radicals include —O—$CH_2OH$, —O—$CH_2CH_2OH$, —O—$CH_2CH_2CH_2OH$, —O—$CH_2CH(OH)CH_3$, —O—$CH_2CH_2CH_2CH_2OH$.

Examples of ($C_1$ to $C_4$)-aminoalkyl radicals include —$CH_2NH_2$, —$CH_2CH_2NH_2$, —$CH_2CH_2CH_2NH_2$, —$CH_2CH(NH_2)CH_3$, —$CH_2CH_2CH_2CH_2NH_2$.

The phenyl group, which may also be substituted, is an example of an aryl group.

Examples of aryl-($C_1$ to $C_4$)-alkyl groups include the benzyl group and the 2-phenylethyl group.

In addition, keratin-containing fibers to be decolored may also be dyed with naturally occurring natural dyes, such as those found in henna red, henna neutral, henna black, chamomile blossoms, sandalwood, black tea, buckthorn bark, sage, logwood (campeachy wood), madder root, catechu, sedre and alkanna root.

Keratin-containing fibers to be decolored may have been dyed either with substantive dyes alone, or with a combination of substantive dyes and oxidative dyes. Preferred suitable substantive dyes include nitrophenylenediamines, nitroaminophenols, azo dyes, anthraquinones or indophenols. Substantive dyes preferably suitable for decoloring include the compounds known by the international designations and/or brand names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 12, Disperse Blue 3, Acid Blue 7, Acid Green 50, HC Violet 1, Disperse Violet 1, Disperse Violet 4, Acid Violet 43, Disperse Black 9, Acid Black 1 and Acid Black 52 as well as 1,4-diamino-2-nitrobenzene, 2-amino-4-nitrophenol, 1,4-bis-(β-hydroxyethyl)amino-2-nitrobenzene, 3-nitro-4-(β-hydroxyethyl)aminophenol, 1,4-bis-(β-hydroxyethyl)amino-2-nitrobenzene, 3-nitro-4-(β-hydroxyethyl)aminophenol, 2-(2'-hydroxyethyl)amino-4,6-dinitrophenol, 1-(T-hydroxyethyl)amino-4-methyl-2-nitrobenzene, 1-amino-4-(2'-hydroxyethyl)amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-1-hydroxy-4-nitrobenzene. Preferred inventive agents are characterized in that they additionally contain at least one substantive dye, preferably in an amount of 0.01 to 20 wt %, based on the total colorant.

Furthermore, keratin-containing fibers to be decolored according to the invention may preferably have been dyed with a cationic substantive dye. Especially preferred here are (a) cationic triphenylmethane dyes such as Basic Blue 7, Basic Blue 26, Basic Violet 2 and Basic Violet 14, (b) aromatic systems substituted with a quaternary nitrogen group such as Basic Yellow 57, Basic Red 76, Basic Blue 99, Basic Brown 16 and Basic Brown 17, as well as (c) substantive dyes containing a heterocycle having at least one quaternary nitrogen atom, such as those mentioned in claims 6 to 11 of EP-A2-998 908.

Preferred cationic substantive dye of group (c) include in particular the following compounds:

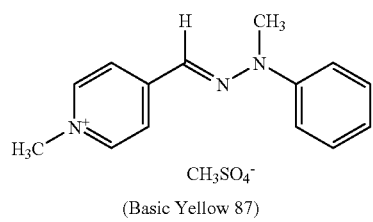
(Basic Yellow 87)

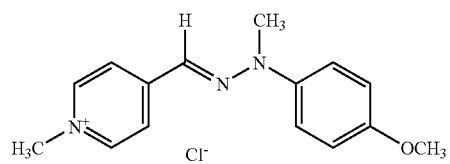

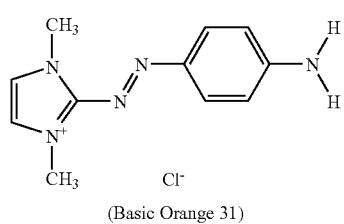
(Basic Orange 31)

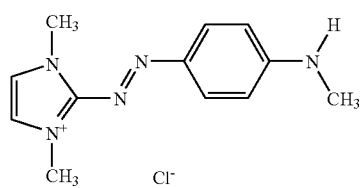

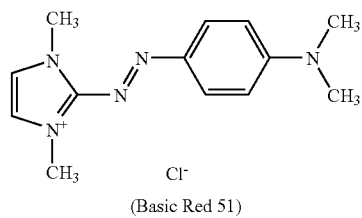
(Basic Red 51)

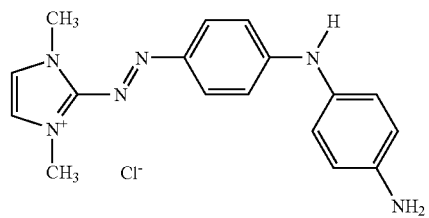

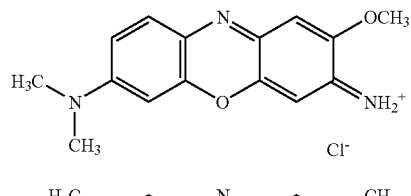

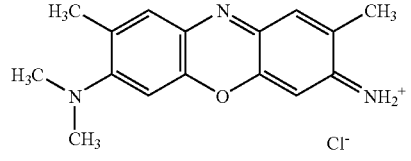

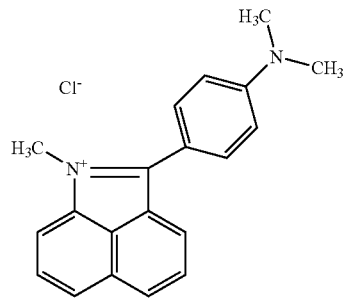

Compounds of formulas (DZ1), (DZ3) and (DZ5) are most especially preferred cationic substantive dyes of group (c). The cationic substantive dyes distributed under the brand name Arianor® are especially preferred suitable substantive dyes according to the invention.

A second subject matter of the invention is the use of an agent according to the first subject matter of the invention for decoloring keratin-containing fibers, in particular human hair.

A third subject matter of the invention is a method for reductive decoloring of keratin-containing fibers, in particular human hair, in which an agent of the first subject matter of the invention is applied to the keratin-containing fibers and is rinsed out again after a treatment time.

The keratin-containing fibers are preferably dyed with oxidative dyes and/or substantive dyes.

The treatment time is preferably 1 to 60 minutes, preferably 5 to 30 minutes. The action of the inventive agent may take place not only at room temperature but preferably in a temperature range from 15° C. to 60° C., in particular from 25° C. to 60° C.

In a preferred embodiment of the method, immediately before applying the inventive agent of the first subject matter of the invention, the ready-to-use agent is prepared by mixing a composition containing, optionally in a cosmetic vehicle, at least one organic compound having at least one thiol group and at least one optionally derivatized carboxy group with a composition containing, in a cosmetic vehicle, at least one organic compound chosen from the group formed by (i) cyclic organic carbonates and
(ii) glycerol and its derivatives, and
(iii) $C_4$-$C_{12}$ fatty acid dimethylamides.

Said compositions may be finished and/or acquired before mixing as described further below.

After completion of the treatment time, the keratin-containing fibers are rinsed out, preferably using a surfactant-containing agent such as a cleaning agent or a shampoo. The substrate may optionally be washed out several times and/or treated with the surfactant-containing agent.

After rinsing out, it may be advantageous to treat the keratin-containing fibers with a composition containing an oxidizing agent. Hydrogen peroxide is the preferred oxidizing agent, preferably being used in concentrations of 0.5 to 6 wt %. The treatment time is preferably 1 to 30 minutes, especially preferably 1 to 10 minutes. After the end of the treatment time, the composition containing the oxidizing agent is rinsed out.

It is preferable according to the invention to prepare the inventive agent as a multicomponent system in the form of a kit. It is preferable to prepare, in a first container, a composition containing, optionally in a cosmetic vehicle, at least one organic compound having at least one thiol group and at least one optionally derivatized carboxy group, and in a separate second container, a composition containing, in a cosmetic vehicle, at least one organic compound chosen from the group formed by (i) cyclic organic carbonates and
(ii) glycerol and its derivatives, and
(iii) $C_4$-$C_{12}$ fatty acid dimethylamides.

According to the invention, containers include bottles, sachets, bags, tubes, cans and many others. A multi-chamber container is also considered to be a container in the sense of the invention. The respective compositions are prepared in different chambers in a multi-chamber container and are brought together and thereby mixed immediately before or after they leave the multi-chamber container.

The composition of the first container is preferably a solid, in particular, a powder, granules or molded bodies.

A powdered composition of the first container has a preferred average particle size of 0.0001 to 100 µm, in particular from 0.005 to 10 µm. These powders may be treated to remove dust by coating with fats, oils or waxes such as silicone oils, liquid hydrocarbons, dialkyl ethers, fatty acids, fatty alcohols.

Granules are understood according to the invention to be granular particles. These granular particles are free flowing.

Granules may be produced by wet granulation, by dry granulation and/or by compacting and by melt-solidification granulation. The most customary granulation technique is wet granulation because this technique is subject to the least restrictions and is the most reliable in yielding granules with favorable properties. Wet granulation is performed by moistening the powder mixtures with solvents and/or solvent mixtures and/or solutions of binders and/or solutions of adhesives and is preferably performed in mixers, fluidized beds or spray towers, where said mixers may be equipped with stirring and kneading tools, for example. However, combinations of fluidized bed(s) and mixer(s) and/or combinations of different mixers may be used for granulation. Granulation is performed under low to high shearing forces.

If the composition of the first container is in the form of molded bodies, then these inventive molded bodies may have any geometric shape, for example, concave, convex, biconcave, biconvex, cubic, tetragonal, orthorhombic, cylindrical, spherical, segmented cylindrical, disk-shaped, tetrahedral, dodecahedral, octahedral, conical, pyramidal, ellipsoidal, pentagonal-prismatic, heptagonal-prismatic and octagonal-prismatic and rhombohedral forms. Completely irregular base areas such as arrow shapes or animal shapes, trees, clouds, etc. may also be implemented. The design as plates, rod and bar shapes, cubes, cuboids and corresponding three-dimensional elements with planar side faces and in particular cylindrical embodiments with a circular or oval cross section and molded bodies with a spherical geometry are preferred according to the invention. Especially preferred are molded bodies in the form of a spherical geometry.

The cylindrical embodiment includes the presentation form, from the tablet to compact cylindrical pieces with a height-to-diameter ratio of greater than 1. If the basic molded body has corners and edges, they are preferably rounded. An embodiment with rounded corners and chamfered ("beveled") edges is preferred as an additional optical differentiation.

In addition to a spherical shape, the spherical embodiment also includes a hybrid of a spherical shape and a cylindrical shape, where each base area of the cylinder is capped with a hemisphere. The hemispheres preferably have a radius of approximately 4 mm, and the entire molded body of this embodiment has a length of 12-14 mm.

An inventive molded body having a spherical embodiment can also be produced according to the known methods. It is possible to produce molded bodies by extrusion of a premix with subsequent shaping, as explained in greater detail in WO-A-91/02047, for example.

In another preferred embodiment, almost spherical molded bodies are therefore produced in particular by extrusion and subsequent rounding for the shaping.

In another embodiment, the portioned pellets may each be designed as separate individual elements corresponding to the predetermined dose quantity of the CH-acidic compounds and/or the reactive carbonyl compounds. Likewise, however, it is possible to form pellets, which combine a plurality of such units of mass in one pellet, whereby in particular through predetermined breaking points, the easy detachability of portioned smaller units is provided. A design of the portioned pellets as tablets in a cylindrical or cubical shape may be expedient, where a diameter/height ratio in the range of approximately 0.5:2 to 2:0.5 is preferred. Conventional hydraulic presses, eccentric presses or rotary presses are suitable devices for producing such pellets in particular.

Another possible three-dimensional shape of the inventive molded bodies has a rectangular base area, where the height of the molded bodies is smaller than the smaller rectangular side of the base area. Rounded corners are preferred in this product form.

Another molded body that can be produced has a plate-shaped or slab-shaped structure with alternating thick, long segments and thin, short segments, so that individual segments can be broken off from this "bar" at the predetermined breaking points, formed by the short, thin segments, and used in portioned amounts in this way. This principle of the "bar-shaped" molded body may also be implemented in other geometric shapes (e.g., right angle triangles), which are connected to one another on the longitudinal sides on only one of their sides.

If the inventive molded bodies contain at least one further component in addition to the coupler component, then in another embodiment it may be advantageous not to press the different components exclusively to form a uniform tablet. In tableting in this embodiment, molded bodies having multiple layers, that is, at least two layers are obtained. It is also possible for these different layers to have different dissolving rates. This can yield advantageous properties of the molded bodies in terms of application technology. For example, if the molded bodies contain components which have negative effects on one another mutually, then it is possible to integrate one component into a more rapidly dissolving layer and to incorporate the other component into a more slowly soluble layer, so that the components do not already react with one another during the dissolving process.

The layered structure of the molded bodies may be that of a stack, whereby a dissolving process of the inner layer(s) already takes place at the edges of the molded body if the outer layers are not yet completely dissolved. With the stacked arrangement, the axis of the stack may be arranged in any manner relative to the axis of the tablet. In the case of a cylindrical tablet, for example, the axis of the stack may thus be parallel or perpendicular to the height of the cylinder.

However, according to another embodiment, it may also be preferable to achieve a complete sheathing of the inner layer(s) by the respective layer(s) situated further toward the outside, thus preventing premature dissolving of components of the inner layer(s). Molded bodies in which the layers are sheathed with the various active ingredients are preferred. For example, a layer (A) may be completely sheathed by the layer (B), which may in turn be completely sheathed by the layer (C). Likewise, molded bodies in which, for example, layer (C) is completely sheathed by layer (B), which is in turn completely sheathed by layer (A), may also be preferred.

Similar effects can also be achieved by coating individual components of the composition to be pressed or the entire molded body. To this end, bodies to be coated may be sprayed with aqueous solutions or emulsions, for example, or a coating may be obtained by melt coating. For example, use of a coating of hydroxypropylmethyl cellulose, cellulose, PEG stearates and colored pigments has proven suitable according to the invention.

The (trough) molded bodies produced according to the invention may be provided entirely or partially with a coating, as described above. Preferred methods according to the invention are those in which an aftertreatment consists of applying a coating layer to the molded body surface(s), in which the filled trough(s) is (are) located, or applying a coating layer to the entire molded body.

An inventive molded body has a preferred breaking hardness of 30-100 N, especially preferably 40-80 N, most especially preferably 50-60 N (measured according to the European Pharmacopoeia 1997, $3^{rd}$ edition, ISBN 3-7692-2186-9 "2.9.8 Breaking strength of tablets" on pp. 143-144 with a Schleuniger 6D tablet hardness tester).

In addition, inventive molded bodies may be a molded body having a trough produced by known tableting methods and described by the term "basic molded body." In this embodiment, the basic molded body is preferably produced first, and then in another operating step, the additional test part is applied to and/or introduced into this basic molded body. The resulting product is referred to below with the generic term "trough molded body" or "trough tablet."

The basic molded body according to the invention may in principle assume any feasible three-dimensional shapes. The three-dimensional shapes already mentioned above are especially preferred. The shape of the trough may be freely selected, but according to the invention, molded bodies in which at least one trough may assume a concave, convex, cubical, tetragonal, orthorhombic, cylindrical, spherical, segmented cylindrical, disk-shaped, tetrahedral, dodecahedral, octahedral, conical, pyramidal, ellipsoidal, pentagonal-prismatic, heptagonal-prismatic and octagonal-prismatic as well as rhombohedral forms are preferred. Completely irregular trough shapes such as arrow shapes or animal shapes, trees, clouds, etc., may also be implemented. As is the case with basic molded bodies, troughs with rounded corners and edges or with rounded corners and beveled edges are preferred.

The size of the trough in comparison with the entire molded body depends on the desired application of the molded body. The size of the trough may vary, depending on whether a smaller or larger amount of active substance is to be contained in the second pressed part. Regardless of the intended purpose, molded bodies in which the weight ratio of the basic molded body to the trough filling is in the range of 1:1 to 100:1, preferably 2:1 to 80:1, especially preferably from 3:1 to 50:1, and in particular from 4:1 to 30:1 are preferred.

Similar statements can also be made about the surface proportions constituted by the basic molded body and/or the trough filling in the total surface area of the molded body. Molded bodies in which the surface area of the pressed trough filling constitutes 1 to 25%, preferably 2 to 20%, especially preferably 3 to 15%, and in particular 4 to 10% of the total surface area of the filled basic molded body are preferred here.

For example, if the total molded body has dimensions of 20×20×40 mm and thus has a total surface area of 40 cm$^2$, then trough fillings having a surface area of 0.4 to 10 cm$^2$, preferably 0.8 to 8 cm$^2$, especially preferably 1.2 to 6 cm$^2$ and in particular 1.6 to 4 cm$^2$ are preferred.

The trough filling and the basic molded body are preferably colored so they can be differentiated visually. In addition to visual differentiation, trough tablets have advantages in terms of applications technology due to different solubilities of the different areas, but also due to the separate layering of the active ingredients in the different areas of the molded bodies.

Molded bodies in which the pressed trough filling dissolves more slowly than the basic molded body are preferred according to the invention. By incorporating certain components, the solubility of the trough filling can be varied in a targeted manner, while the release of certain ingredients from the trough filling can lead to advantages in the dyeing process. Ingredients localized preferably at least proportionally in the trough filling include, for example, the conditioning active ingredients, oil substances, vitamins and plant-based active ingredients described in the "Additional components" paragraph.

It may be preferred according to the invention to separately encapsulate individual active ingredients before incorporating them into the molded bodies. Thus, for example, it is conceivable to use especially reactive components or even scents in encapsulated form.

Inventive molded bodies are produced by first dry mixing the ingredients, which may be partially or completely pre-granulated, and then introducing them into the mold, in particular pressing them to form tablets based on known methods. To produce the inventive molded bodies, the premix is compressed between two rams in a so-called female die to form a solid compressed tablet. This procedure, which is referred to below simply as tableting, is divided into four phases: dosing, compaction (elastic deformation), plastic deformation and ejection.

The premix is first introduced into the female die, where the filling quantity and thus the weight and shape of the resulting molded body are determined by the position of the bottom ram and the shape of the die. Uniform dosing is preferably also achieved at a high throughput of molded bodies by means of volumetric dosing of the premix. In the remaining course of tableting, the top ram touches the premix and continues to lower itself in the direction of the bottom ram. In this compaction, the particles of the premix are pressed closer and closer together, while the cavity volume within the filling between the rams decreases continuously. Plastic deformation, in which the particles flow together and the molded body is formed, begins beyond a certain position of the top ram (and thus beyond a certain pressure on the premix). Depending on the physical properties of the premix, a portion of the premix particles are also crushed, and sintering of the premix occurs at even higher pressures. With an increase in pressing rate (i.e., at high throughput quantities), the phase of elastic deformation becomes progressively shorter, so the resulting molded bodies may have more or less large cavities. In the last step of tableting, the finished molded body is forced out of the female die by the bottom ram and conveyed away by the downstream conveyance equipment. At this point in time, only the weight of the molded body is determined definitively because the pellets may still change their shape and size due to physical processes (recovery, crystallographic effects, cooling, etc.).

Tableting is performed in commercial tablet presses, which may be equipped with single or double rams. In the latter case, not only the top ram is used to build up the pressure but also the bottom ram moves toward the top ram during the pressing operation, while the top ram is pushing downward. For all production quantities, preferably eccentric tableting presses are used in which the ram(s) is (are) attached to an eccentric cam, which is in turn mounted on an axle having a certain circumferential velocity. The movement of these ram presses is comparable to the operation of a conventional four-cycle engine. Compression may be accomplished with one top ram and one bottom ram, but multiple rams may also be attached to an eccentric ram, in which case the number of bores in the female die is increased accordingly. The throughput of eccentric presses varies from a few hundred to max. 3000 tablets per hour, depending on the type of press.

For larger throughputs, rotary tablet presses on which a large number of female dies are arranged in a circle on a so-called die plate are selected. The number of female dies varies between 6 and 55, depending on the model, but even larger female dies are available commercially. Each female die on the die plate is assigned a top ram and a bottom ram, where again the applied pressure can be built up actively only by the top ram and/or bottom ram but also by the two rams together. The die plate and the rams move about a shared vertical axis, the rams being brought into the positions for filling, compaction, plastic deformation and ejection with the help of rail-type curved paths during revolution. At the locations where an especially important lifting and/or lowering of the rams is required (filling, compaction, ejection), these curved paths are supported by additional low-pressure parts, pull-down rails and trenching paths. The female die is filled by means of a rigidly arranged feed mechanism, the so-called filling spout, which is connected to a storage container for the premix. The applied pressure on the premix is individually adjustable via the press paths for the top ram and the bottom ram, such that the pressure buildup is accomplished by rolling the ram shaft heads past adjustable pressure rollers.

Rotary presses may also be provided with two filling spouts to increase throughput, in which case only a semicircle need be traveled to produce one tablet.

To produce two-layer and multilayer molded bodies, multiple filling spouts are arranged one after the other without ejecting the slightly pressed first layer before further filling. Through suitable process management, jacketed tablets and spot tablets having an onion-layer-type design can be produced; in the case of spot tablets, the top side of the core and/or the core layers is/are not covered and thus remain(s) visible. Rotary tablet presses can also be equipped with single or multiple dies, so that an outer circle with 50 bores and an inner circle with 35 bores, for example, may be used for pressing at the same time. Throughputs of modern rotary tablet presses amount to more than one million molded bodies per hour.

In tableting with rotary presses, it has proven advantageous to perform the tableting with the least possible fluctuations in the weight of the tablet. In this way, fluctuations in hardness of the tablet can also be reduced. Minor fluctuations in weight may be achieved in the following way:

using plastic inserts with small thickness tolerances,
low rotational speed of the rotor,
large filling spouts,
coordinating the rotational speed of the filling spout wing with the rotational speed of the rotor,
filling spout having a constant powder height, and/or
decoupling of the filling spout and the powder supply.

To reduce caking on the ram, antistick coatings known from the art can be applied. Especially advantageous are plastic coatings, plastic inserts or plastic rams. Rotating rams have also proven to be advantageous, where the top ram and the bottom ram is designed to rotate, if possible. With rotating rams, it is not usually necessary to have a plastic insert. In this case, the ram surfaces should be electropolished.

It has also been found that long pressing times are advantageous. These may be achieved with pressure rails, multiple pressure rolls or low rotational speeds of the rotor. Since fluctuations in hardness of the tablet are caused by fluctuations in pressing forces, systems which limit the pressing force should be used. Elastic rams, pneumatic compensators or resilient elements in the force path may be used here. The pressure roll may also be designed to be resilient.

Tableting machines that are suitable within the scope of the present invention are obtainable, for example, from the companies Apparatebau Holzwarth GbR, Asperg, Wilhelm Fette GmbH, Schwarzenbek, Fann Instruments Company, Houston, Tex. (USA), Hofer GmbH, Weil, Horn & Noack Parmatechnik GmbH, Worms, IMA Verpackungssysteme GmbH Viersen, KILIAN, Cologne, KOMAGE, Kell am See, KORSCH Pressen AG, Berlin as well as Romaco GmbH, Worms. Additional suppliers include, for example, Dr. Herbert Pete, Vienna (AT), Mapag Maschinenbau AG, Bern (CH), BWI Manesty, Liverpool (GB), I. Holand Ltd., Nottingham (GB), Courtoy, N.V., Halle (BE/LU) as well as Mediopharm Kamnik (SI). Especially suitable is, for example, the HPF 630 hydraulic double pressure press from LAEIS, D. Tableting molds are available, for example, from Adams Tablettierwerkzeuge [tableting molds], Dresden, Wilhelm Fett GmbH, Schwarzenbek, Klaus Hammer, Solingen, Herber & Sohne GmbH, Hamburg, Hofer GmbH, Weil, Horn & Noack, Pharmatechnik GmbH, Worms, Ritter Pharmatechnik GmbH, Hamburg, Romaco, GmbH, Worms and Notter Werkzeugbau, Tamm. Other suppliers include Senss AG, Reinach (CH) and Medicopharm, Kamnik (SI).

The method for manufacturing the molded bodies, however, is not limited to just pressing one particular premix to form a molded body. Instead, this method may also be expanded, so that multilayer molded bodies are manufactured in an essentially known way by preparing two or more premixes, which are pressed in succession. In doing so, the premix that is added first is slightly prepressed to yield a smooth top side running parallel to the bottom of the molded body, and then after adding the second premix, the final pressure is performed to yield the finished molded body. In the case of molded bodies having three or more layers, another prepressing is performed after each addition of premix before performing the final pressing to yield the molded bodies after addition of the last premix.

Pressing of the particulate composition into the trough may be performed on tableting presses as in production of the basic molded bodies. In a preferred procedure, the basic molded bodies with a trough are produced first, then filled and next pressed again. This may be accomplished by ejecting the basic molded bodies out of a first tablet press, then filling and conveying them to a second tablet press, where the final pressing is performed. Alternatively, the final pressing may also be performed by pressure rollers, which roll over the molded bodies on a conveyor belt. However, it is also possible to provide a rotary tableting press having different sets of rams, so that a first set of rams presses recesses into the molded bodies, and the second set of rams ensures a flat surface of the molded bodies by pressing again after filling.

Regardless of its appearance as a powder, granules and/or molded bodies, the composition of the first container preferably contains at least one of the following additives described below.

The composition of the first container preferably also contains at least one dissolving accelerator. This is preferred in particular when the composition of the first container is in granulated form or as molded bodies. The term "dissolving accelerator" comprises gas-evolving components, preformed and enclosed gases, and disintegrants as well as mixtures thereof.

In a first embodiment of the present invention, gas-evolving components are used as the dissolving accelerator. These components react with one another on coming in contact with water with in-situ formation of gases, which then create a pressure in the tablet, causing the tablet to disintegrate into smaller particles. Special combinations of suitable acids with bases are one example of such a system. Monovalent, divalent or trivalent acids having a $pK_a$ value of 1.0 to 6.9 are preferred. Preferred acids include citric acid, malic acid, maleic acid, malonic acid, itaconic acid, tartaric acid, oxalic acid, glutaric acid, glutamic acid, lactic acid, fumaric acid, glycolic acid and mixtures thereof. Citric acid is especially preferred. It may be most especially preferable to use citric acid in particulate form, with particles having a diameter of less than 1000 µm, in particular less than 700 µm, most especially preferably less than 400 µm. Other alternative suitable acids include the homopolymers or copolymers of acrylic acid, maleic acid, methacrylic acid or itaconic acid with a molecular weight of 2000 to 200,000. Homopolymers of acrylic acid and copolymers of acrylic acid and maleic acid are especially preferred. Preferred bases according to the invention include alkali metal silicates, carbonates, bicarbonates and mixtures thereof. Metasilicates, bicarbonates and carbonates are especially preferred but bicarbonates are most especially preferred. Particulate bicarbonates having a particle diameter of less than 1000 µm, in particular less than 700 µm, most especially preferably less than 400 µm are especially preferred. Sodium or potassium salts of the aforementioned bases are especially preferred. These gas-evolving components are preferably contained in the inventive dye moldings in an amount of at least 10 wt %, in particular at least 20 wt %.

In another embodiment of the present invention, the gas is preformed or is enclosed, so that when using the dissolution of the molded body, the evolution of gas begins and further dissolution is accelerated. Examples of suitable gases include air, carbon dioxide, $N_2O$, oxygen and/or other nontoxic nonflammable gases.

In an especially preferred embodiment of the present invention, disintegration aides, so-called disintegrants, are incorporated into the composition of the first container as dissolving accelerators to shorten the decomposition times. This is especially preferred when the composition of the first container is in the form of molded bodies or granules. Disintegrants and/or decomposition accelerators are understood according to Römpp ($9^{th}$ edition, Vol. 6, p. 4440) and Voight *Textbook of Pharmaceutical Technology* ($6^{th}$ edition 1987, pp. 182-184) to be excipients which ensure the rapid disintegration of solid agglomerates (i.e., in particular molded bodies) in water or gastric fluid and ensure the release of the pharmaceuticals in reabsorbable form.

These substances, which are also known as disintegrants based on their effect, increase their volume (swelling) on admission of water. Swelling disintegration aids include, for example, synthetic polymers such as polyvinylpyrrolidone (PVP) or natural polymers and/or modified natural substances, such as cellulose and starch and their derivatives, alginates or casein derivatives.

Within the scope of the present invention, cellulose-based disintegrants are preferred disintegrants, so that preferred compositions of the first container, in particular when it is in the form of molded bodies, contain cellulose-based disintegrants in amounts of 0.5 to 70 wt % preferably 3 to 30 wt %, based on total composition of the first container. Pure cellulose has the formal empirical composition $(C_6H_{10}O_5)_n$ and formally is a β-1,4-polyacetal of cellobiose, which in turn comprises two molecules of glucose. Suitable celluloses consist of approximately 500 to 5000 glucose units and consequently have average molecular weights of 50,000 to 500,000. Within the scope of the present invention, cellulose derivatives obtainable by polymer-like reactions from cellulose may also be used as cellulose-based disintegrants. Such chemically modified celluloses include esterification and/or etherification products, in which hydroxy hydrogen atoms have been substituted. However, celluloses in which the hydroxy groups have been replaced by functional groups not bound by an oxygen atom can also be used as cellulose derivatives. For example, alkali celluloses, carboxymethyl cellulose (CMC), cellulose esters and ethers as well as amino celluloses fall in the group of cellulose derivatives. The aforementioned cellulose derivatives are preferably not used as the single cellulose-based disintegrant but instead are used in mixture with cellulose. The cellulose derivative content of these mixtures is preferably less than 50 wt %, especially preferably less than 20 wt %, based on the cellulose-based disintegrant. Pure cellulose, which is free of cellulose derivatives, is especially preferred as a cellulose-based disintegrant.

Cellulose used as a disintegration aid cannot be used in finely divided form according to the invention but instead must be converted to a coarser form (e.g., granulated or compacted) before being added to premixes to be compressed. The particle sizes of such disintegrants are usually above 200 µm; preferably at least 90 wt % is between 300 and 1600 µm and in particular at least 90 wt % is between 400 and 1200 µm. Disintegration aids are available commercially under the brand name Arbocel® from the company Rettenmaier, for example. A preferred disintegration aid is Arbocel® TF-30-HG, for example.

Microcrystalline cellulose can be used as a preferred cellulose-based disintegrant or as an ingredient of these components. Microcrystalline cellulose is obtained by partial hydrolysis of celluloses under such conditions which attack only the amorphous regions (approximately 30% of the total cellulose mass) of the celluloses and dissolve it completely, but leave the crystalline regions (approximately 70%) undamaged. A subsequent deaggregation of the microfine celluloses formed by hydrolysis yields microcrystalline celluloses, which have primary particle sizes of approximately 5 μm and may be compacted to form granules with an average particle size of 200 μm, for example. Suitable microcrystalline cellulose is available commercially under the brand name Avicel®.

Accelerated dissolution of the composition of the first container can also be achieved according to the invention by pregranulation of the additional ingredients.

In a preferred embodiment of the inventive compositions of the first container, they contain a mixture of starch and at least one saccharide in addition to at least one cellulose-based disintegrant for accelerating dissolution. Disaccharides are preferred saccharides of this embodiment for use here. Said mixture is preferably present in the composition of the first container in a weight ratio of starch and the saccharides used of 10:1 to 1:10, especially preferably from 1:1 to 1:10, most especially preferably from 1:4 to 1:8.

Disaccharides that are used are preferably selected from lactose, maltose, sucrose, trehalose, turanose, gentiobiose, melibiose and cellobiose. Especially preferred are lactose, maltose and sucrose and most especially preferred is lactose for use in the inventive molded bodies.

The starch-saccharide mixture is contained in the composition of the first container in an amount of 5 to 70 wt %, preferably 20 to 40 wt %, based on mass of the total agent A.

The composition of the second container preferably comprises a cosmetic vehicle which is liquid under use conditions. This is true in particular when the composition of the first container is in the form of a powder, granules or molded bodies.

The kit may additionally contain application aids such as a brush or mascara brush.

The kit may additionally contain protective gloves.

The kit may also additionally contain a conditioner and/or a shampoo.

Definitions and embodiments mentioned within the scope of the first subject matter of the invention also apply, mutatis mutandis, to the subject matters two to three of the invention.

The subject matter of the invention shall now be explained as an example on the basis of the following embodiments.

EXAMPLES

1. Preparation of the Formulations

The raw material Natrosol 250® HHR was preswollen in water. The raw materials Brij® 30 and Eumulgin® L and/or Cremophor® CO 40, Eumulgin® L and Euxyl® PE 9010 were mixed and then the propylene carbonate was stirred into the mixture. This mixture was then added to the swollen Natrosol while stirring. Immediately before applying to dyed hair, a mixture of L-cysteine hydrochloride monohydrate and oxalic acid was added.

The quantitative amounts are given in percent by weight (wt %) based on the weight of the respective agent.

TABLE 1

| | Formulations | | | | |
|---|---|---|---|---|---|
| Raw material | E1 | E2 | E3 | V1 | V2 |
| L-Cysteine hydrochloride monohydrate | 3.00 | 3.00 | 3.00 | 3.00 | — |
| Propylene carbonate | 20.00 | 20.00 | 20.00 | — | 20.00 |
| Oxalic acid | 1.00 | 1.00 | — | 1.00 | 1.00 |
| Ascorbic acid | — | — | 1.00 | — | — |
| Brij ® 30 [1] | 2.00 | — | 2.00 | 2.00 | 2.00 |
| Cremophor ® CO 40 [2] | — | 2.00 | — | — | — |
| Euxyl ® PE 9010 [3] | — | 1.00 | — | — | — |
| Eumulgin ® L [4] | 2.00 | 2.00 | 2.00 | 2.00 | 2.00 |
| Natrosol ® 250 HHR [5] | 1.25 | 1.25 | 1.25 | 1.25 | 1.25 |
| Water | to 100 | to 100 | to 100 | to 100 | to 100 |

[1] Dodecyl alcohol ethoxylated with four units of ethylene oxide (100 wt % active substance; INCI designation laureth-4) (Unichema)
[2] Hydrogenated castor oil with approximately 40-45 EO units (100 wt % active substance; INCI designation: PEG-40 hydrogenated castor oil) (BASF)
[3] Mixture of 90 wt % 2-phenoxyethanol and 10 wt % 3-(2-ethylhexyloxy)-1,2-propanediol (100 wt % active substance, INCI designations: phenoxyethanol, ethylhexyl glycerin) (Schülke & Mayr)
[4] Lauryl glycol ether, ethoxylated with one unit of propylene oxide and nine units of ethylene oxide (INCI designation: PPG-1-PEG-9 lauryl glycol ether) (Cognis)
[5] Hydroxyethyl cellulose (INCI designation: hydroxyethyl cellulose) (Hercules)

2. Decoloration Tests

Two parts by weight of the respective colorants listed in Table 2 with the brand name Igora Royal (Schwarzkopt) were used for dyeing at room temperature and 30 minutes treatment time on one part by weight hair (Hohenschildt, Berlin). The hair was then rinsed and dried. Next the strands were measured by colorimetry using a Datacolor SF 6000X (Datacolor) and their color intensity was determined as the reference value (dyed strands=color intensity corresponds to 100%).

For each colorant, 12 strands of hair were dyed. All values for color intensity before and after decoloration were averaged (arithmetic mean). Next, four of the dyed hair strands per decoloring agent E1, V1 and V2 were decolored under the same conditions. The strands were rinsed with water and dried. Next, the residual color intensity was again determined by colorimetry after decoloring. Table 2 summarizes the residual color intensities.

TABLE 2

Residual color intensities after decoloration in percentage relative to the color intensity of the starting dyeing

| Colorant | E1 | V1 | V2 |
|---|---|---|---|
| Igora Royal 6-0 | 48.22 | 59.72 | 70.82 |
| Igora Royal 6-7 | 28.38 | 39.92 | 75.82 |
| Igora Royal 6-888 | 46.33 | 57.04 | 59.75 |
| Igora Royal 4-90 | 40.58 | 80.69 | 84.16 |
| Igora Royal 0-77 | 22.04 | 51.08 | 50.45 |

It can be seen clearly here that the residual color intensities of the hair strands treated with the inventive decoloring agent in comparison with the agents of the prior art turn out to be much lower. The decoloring power of the inventive decoloring agent is consequently greater.

Decoloration with the agents E2 and E3 is comparable to that of the agent E1.

We claim:

1. Agent for reductive decoloration of keratin-containing fibers comprising in a vehicle an active ingredient combination of
   (a) at least one organic compound having at least one thiol group and at least one optionally derivatized carboxyl group,
   (b) at least one cyclic organic carbonate, of formula (II-1)

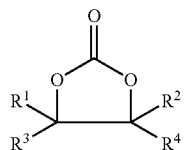

(II-1)

wherein one of $R_1$, $R_2$, $R_3$ and $R_4$ is methyl and the remainder are hydrogen, wherein the compounds of component (b) are present in an amount of 5 wt % to 50 wt %, each based on total weight of the agent, and
   (c) oxalic acid.

2. Agent according to claim 1, wherein component (a) is selected from at least one compound of formula (I)

$$HS-X-COOM \qquad (I)$$

wherein
   X is a saturated or unsaturated, linear or branched and aliphatic hydrocarbon structure optionally substituted with at least one of a thiol, carboxyl, carboxylate, hydroxy, $NH_2$, ($C_1$ to $C_6$)-alkylamino, ($C_1$ to $C_6$)-dialkylamino, and/or ($C_1$ to $C_6$)-hydroxyalkyl, and
   M is hydrogen, a $C_1$ to $C_8$ alkyl group or an equivalent of a monovalent or polyvalent cation.

3. Agent according to claim 1, wherein component (a) is chosen from at least one representative of the group formed from L-cysteine (acid or salt), D-cysteine (acid or salt), D,L-cysteine (acid or salt), cysteamine and acetylcysteine.

4. Agent according to claim 1, wherein the compounds of component (a) are present in an amount of 1 to 10 wt %, in each based on total weight of the agent.

5. Agent according to claim 1, wherein the agent has a pH of from 1 to 9.

6. Agent according to claim 1, further comprising at least one reductone.

7. Agent according to claim 1, further comprising at least one thickening polymer.

8. Method for reductive decolorization of keratin-containing fibers, comprising applying an agent according to claim 1 to the keratin-containing fibers and rinsing off the agent after a treatment time.

* * * * *